(12) United States Patent (10) Patent No.: US 8,511,183 B2
Lineman et al. (45) Date of Patent: Aug. 20, 2013

(54) GLASS SAMPLING APPARATUS AND METHOD FOR USING SAME TO OBTAIN A GLASS SAMPLE FROM A GLASS MELTING VESSEL

(75) Inventors: David M. Lineman, Painted Post, NY (US); Jason M. McLaughlin, Beaver Dams, NY (US); Matthew C. Morse, Campbell, NY (US); Steven R. Moshier, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 106 days.

(21) Appl. No.: 13/189,971

(22) Filed: Jul. 25, 2011

(65) Prior Publication Data

US 2013/0025379 A1 Jan. 31, 2013

(51) Int. Cl.
*G01N 1/14* (2006.01)
(52) U.S. Cl.
USPC ...................................... 73/864.34
(58) Field of Classification Search
None
See application file for complete search history.

(56) References Cited

U.S. PATENT DOCUMENTS 5,421,215 A 6/1995 Cure et al. ................. 73/864.53

FOREIGN PATENT DOCUMENTS

| JP | 3-259727 | * 11/1991 |
| JP | 2002-071888 | 3/2002 |
| JP | 2008-216171 | 9/2008 |

OTHER PUBLICATIONS

K.K. Vilnis, et al., "An Instrument for Glass Sampling in Depth," *Glass and Ceramics*, Jun. 1959, vol. 16, No. 6, pp. 339-341.

* cited by examiner

*Primary Examiner* — Robert R Raevis
(74) *Attorney, Agent, or Firm* — Thomas R. Beall; William J. Tucker, Esq.

(57) ABSTRACT

A glass sampling apparatus and a method for using the glass sampling apparatus to obtain a glass sample from molten glass within a glass melting vessel are described herein. In one embodiment, the glass sampling apparatus includes: (a) a sampling tube having a first end and a second end, where the second end is used to obtain the glass sample from the molten glass in the glass melting vessel; (b) a first valve; (c) a vacuum device; and (d) a tube network that couples the first end of the sampling tube to both the first valve and the vacuum device.

17 Claims, 21 Drawing Sheets

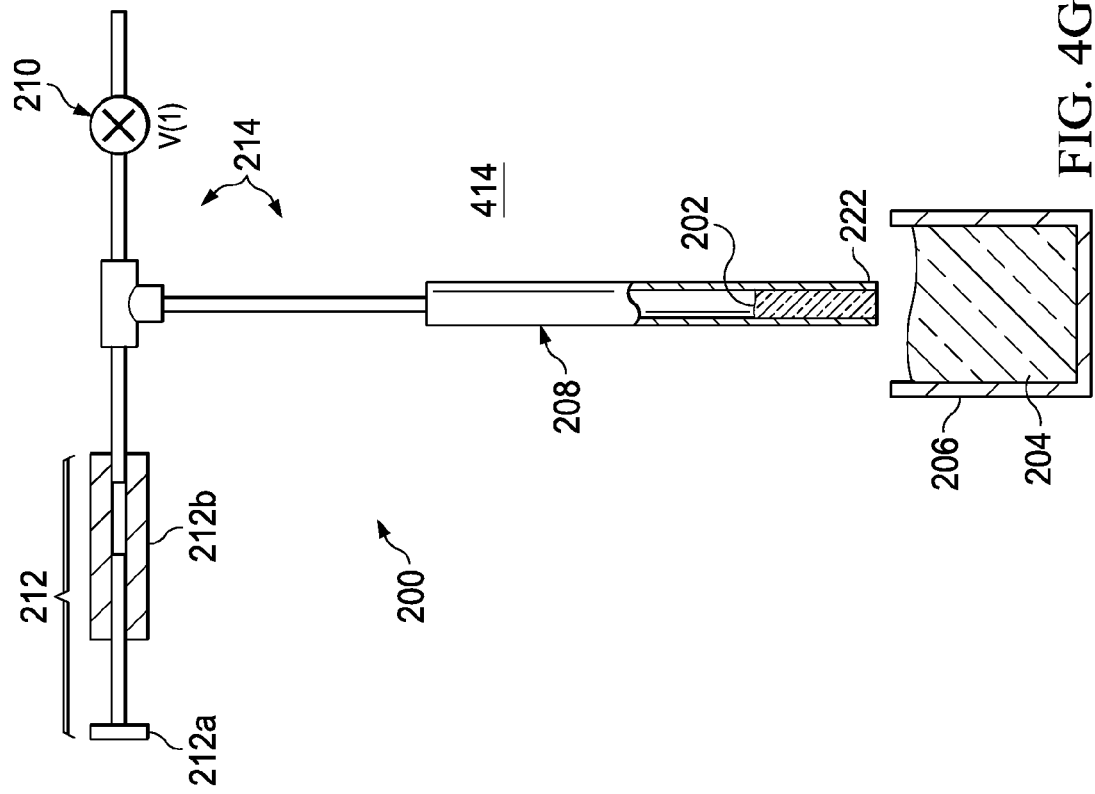
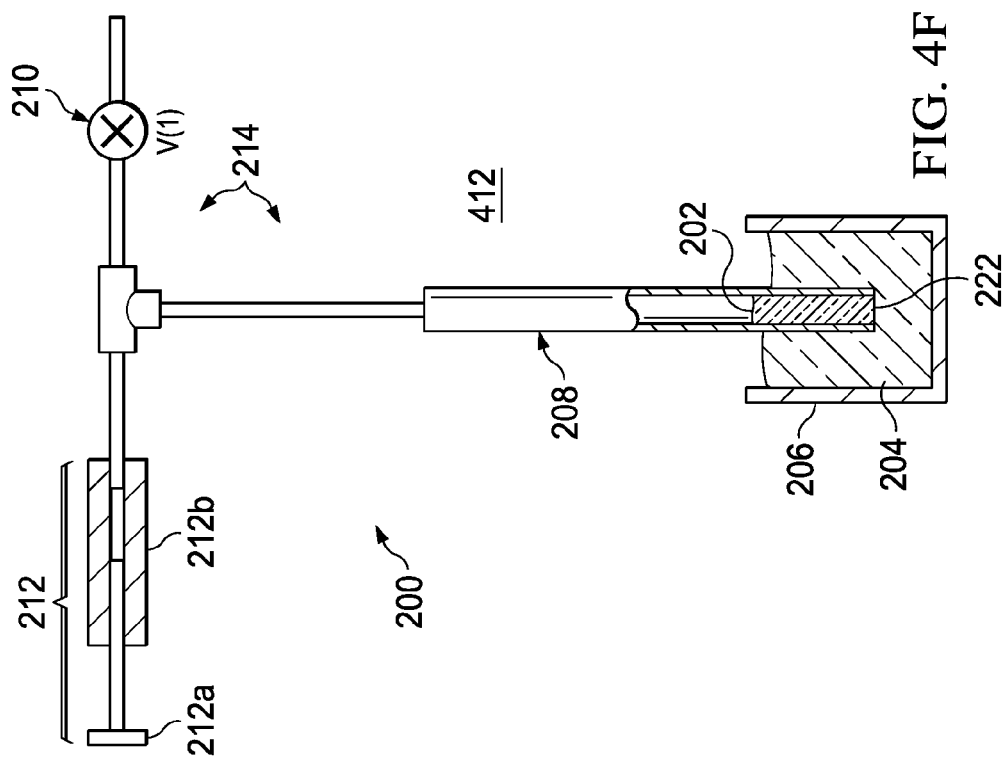

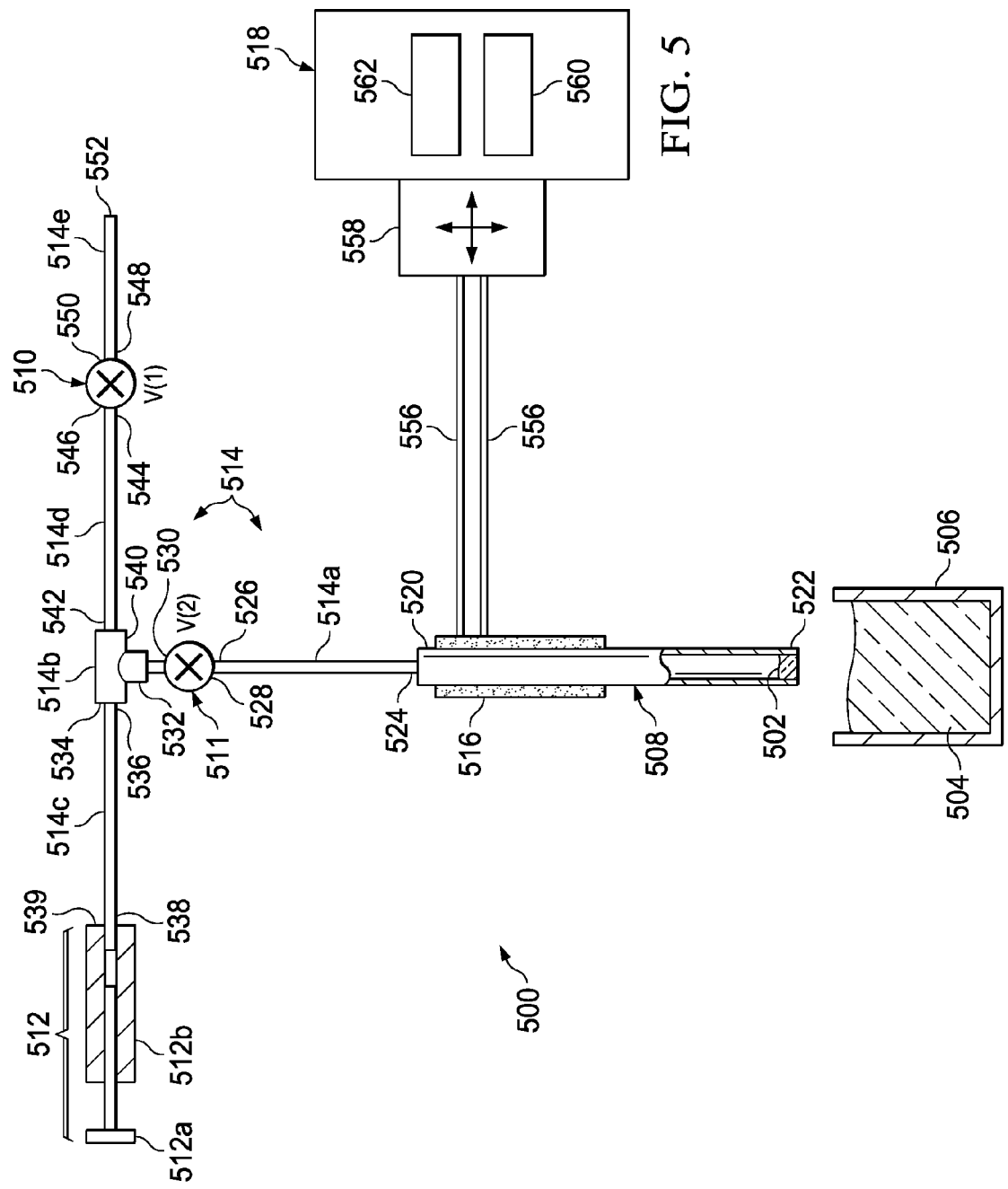

GLASS SAMPLING APPARATUS AND METHOD FOR USING SAME TO OBTAIN A GLASS SAMPLE FROM A GLASS MELTING VESSEL

TECHNICAL FIELD

The present invention relates to a glass sampling apparatus and a method for using the glass sampling apparatus to obtain a glass sample from molten glass within a glass melting vessel.

BACKGROUND

Referring to FIG. 1A (PRIOR ART), there is a schematic of a traditional glass sampling apparatus 100 configured to obtain a glass sample 102 from molten glass 104 within a glass melting vessel 106. The traditional glass sampling apparatus 100 includes a sampling rod 108 that has a first end 110 and a second end 112. The sampling rod 108 is typically two or three feet long and is usually made from quartz. In operation, the user picks an area in the glass melting vessel 106 where they want to obtain the glass sample 102 and then inserts the sampling rod's second end 112 into the selected area of molten glass 104. Basically, the user pushes the sampling rod's second end 112 into the molten glass 104 and then waits to let the glass settle around the second end 112. Then, the user pulls the sampling rod 108 with the glass sample 102 hopefully located thereon up and out from the molten glass 104.

Referring to FIG. 1B (PRIOR ART), there is a photo of two glass samples 102a and 102b obtained from a level probe standpipe in a glass manufacturing system by using the traditional glass sampling apparatus 100. The glass samples 102a and 102b were obtained to determine the glass quality in the level probe standpipe. Unfortunately, the small size of the glass samples 102a and 102b which together had a total weight of 2 grams and their irregular shapes made it very difficult to determine if any defects were present in the glass. Thus, it was not possible to use the glass samples 102a and 102b to estimate the total inclusion level in the system. Accordingly, there is and has been a need to overcome this shortcoming and other shortcomings in order to obtain suitable glass samples from the level probe standpipe or any type of glass melting vessel. This need and other needs have been satisfied by the glass sampling apparatus and method of the present invention.

SUMMARY

A glass sampling apparatus and a method for using the glass sampling apparatus to obtain a glass sample from molten glass within a glass melting vessel are described in the independent claims of the present application. Advantageous embodiments of the glass sampling apparatus and the method for using the glass sampling apparatus to obtain a glass sample from molten glass within a glass melting vessel are described in the dependent claims.

In one aspect, the present invention provides a glass sampling apparatus for obtaining a glass sample from molten glass in a glass melting vessel. The glass sampling apparatus comprises: (a) a sampling tube having a first end and a second end, where the second end is used to obtain the glass sample from the molten glass in the glass melting vessel; (b) a first valve; (c) a vacuum device; and (d) a tube network that couples the first end of the sampling tube to both the first valve and the vacuum device. In addition, the glass sampling apparatus may further include a second valve which is coupled by the tube network between the first end of the sampling tube and both of the first valve and the vacuum device.

In another aspect, the present invention provides a method for obtaining a glass sample from molten glass in a glass melting vessel. The method comprises the steps of: (a) providing a glass sampling apparatus comprising: (i) a sampling tube having a first end and a second end, where the second end is used to obtain the glass sample from the molten glass in a glass melting vessel; (ii) a first valve; (iii) a vacuum device; and (iii) a tube network that couples the first end of the sampling tube to both the first valve and the vacuum device; and (b) obtaining the glass sample from the molten glass in the glass melting vessel using the glass sampling apparatus. In addition, the glass sampling apparatus may further include a second valve which is coupled by the tube network between the first end of the sampling tube and both of the first valve and the vacuum device.

Additional aspects of the invention will be set forth, in part, in the detailed description, figures and any claims which follow, and in part will be derived from the detailed description, or can be learned by practice of the invention. It is to be understood that both the foregoing general description and the following detailed description are exemplary and explanatory only and are not restrictive of the invention as disclosed.

BRIEF DESCRIPTION OF THE DRAWINGS

A more complete understanding of the present invention may be had by reference to the following detailed description when taken in conjunction with the accompanying drawings wherein:

FIGS. 4A-4G are several diagrams used to explain the sequence of steps about how the glass sampling apparatus shown in FIG. 2 can be used to obtain the glass sample (non-surface molten glass and non-near surface molten glass) from the molten glass within the glass melting vessel in accordance with another embodiment of the present invention;

FIG. 5 is a schematic of another glass sampling apparatus in accordance with an embodiment of the present invention;

Figure 1A:
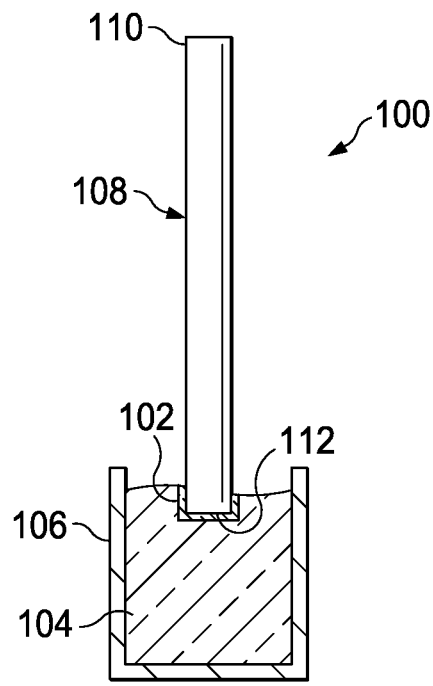
FIGS. 1A-1B (PRIOR ART) respectively illustrate a schematic view of traditional glass sampling apparatus and a photo of two glass samples obtained from a glass melting vessel (e.g., level probe standpipe) using the traditional glass sampling apparatus.
Figure 1B:
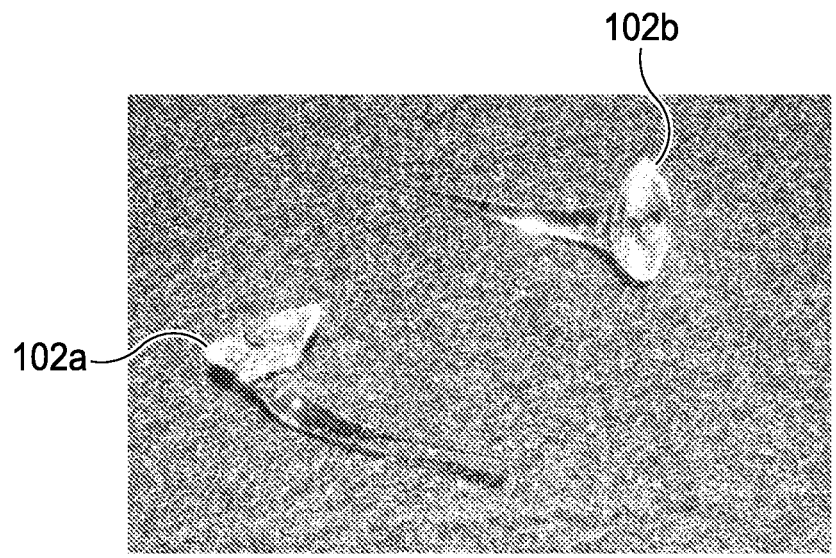
Figure 2:
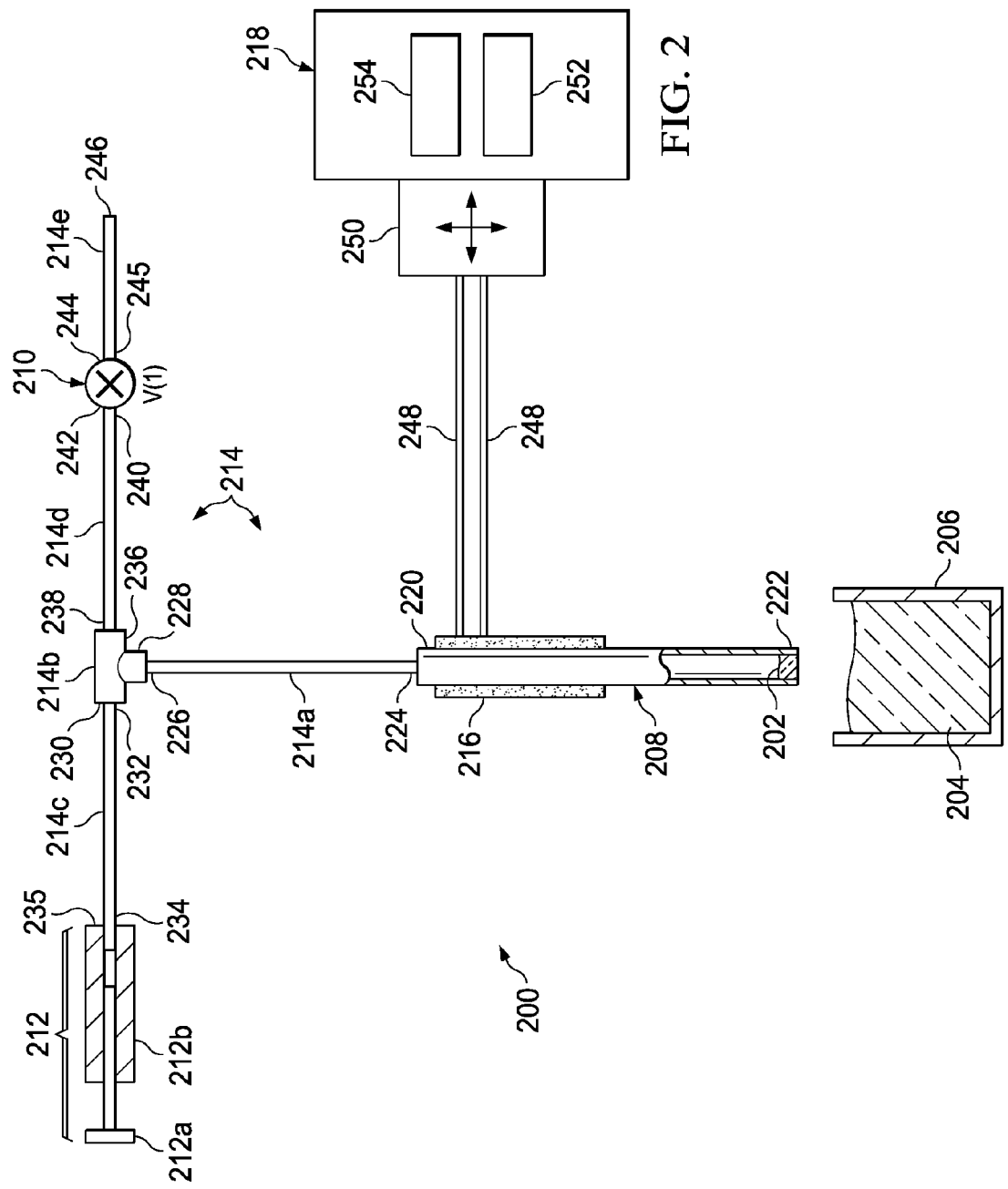
FIG. 2 is a schematic of a glass sampling apparatus in accordance with an embodiment of the present invention.
Figure 8:
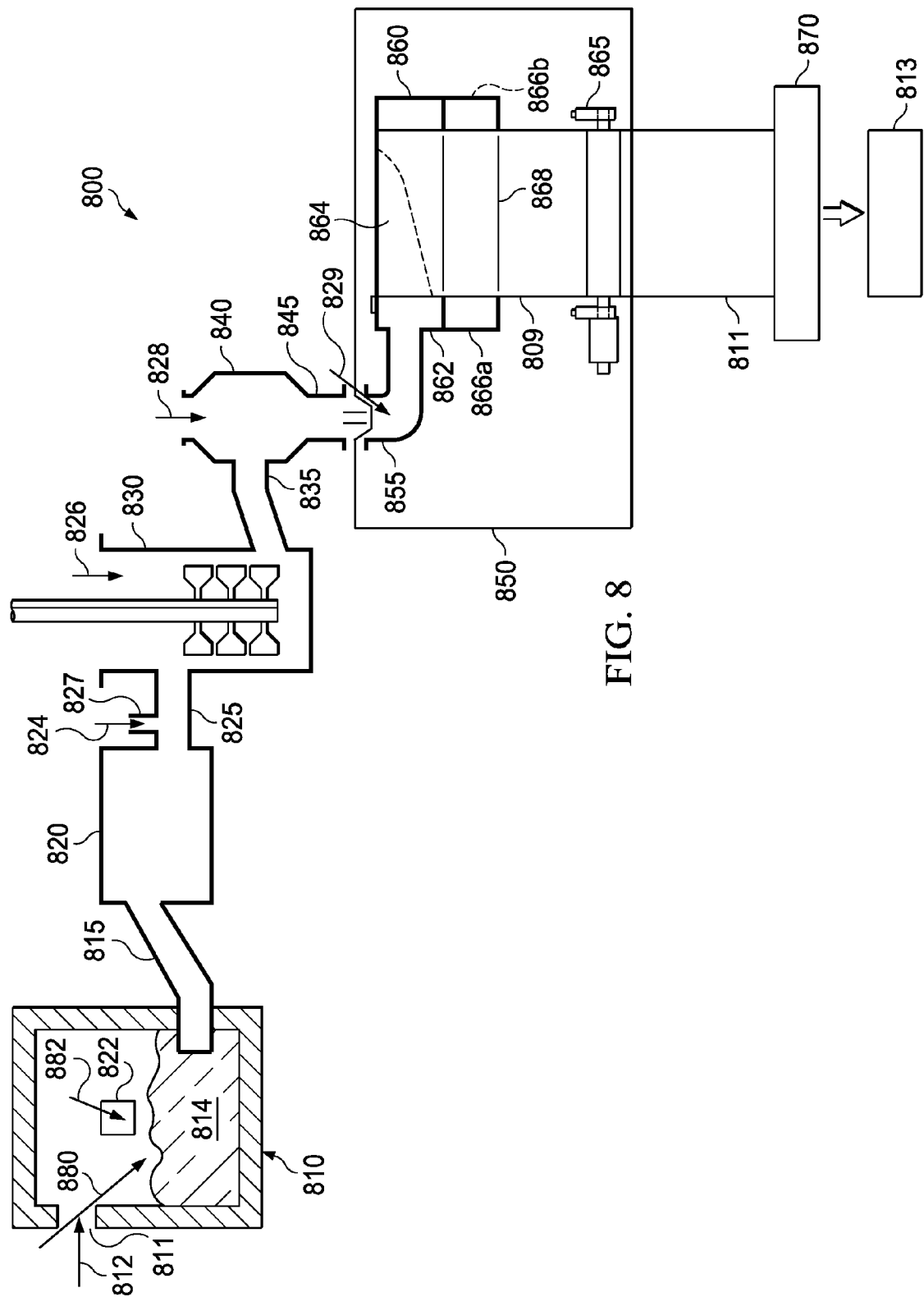

from the molten glass within the glass melting vessel in accordance with another embodiment of the present invention;

FIG. 8 is a schematic view of an exemplary glass manufacturing system which has several glass melting vessels from which the glass sampling apparatus shown in FIGS. 2 and 5 can be used to obtain a glass sample therefrom in accordance with an embodiment of the present invention; and FIGS. 9A-9G are several photos of an exemplary glass sampling apparatus similar to the one shown in FIG. 5 being used to obtain a glass sample from a research scale level probe standpipe in accordance with an embodiment of the present invention.

DETAILED DESCRIPTION

Referring to FIG. 2, there is a schematic of a glass sampling apparatus 200 configured to obtain a glass sample 202 from molten glass 204 within a glass melting vessel 206 in accordance with an embodiment of the present invention. The glass sampling apparatus 200 includes a sampling tube 208, a first valve 210 (e.g., first ball valve 210), a vacuum device 212 (e.g., plunger 212a and syringe 212b), a tube network 214 (e.g., four tubes 214a, 214c, 214d and 214e, and a T-shaped fitting 214b), an electrical isolation sleeve 216 (optional), and a three-axis positioning stage 218 (optional).

The sampling tube 208 (sampling pipe 208) has a first end 220 and a second end 222, where the second end 222 is used to obtain the glass sample 202 from the molten glass 204 within the glass melting vessel 206. The sampling tube 208 can be any length depending on the location of sampling area and made from quartz, platinum, rhodium, palladium, iridium, rhenium, ruthenium, osmium, other refractory tube material, or some combination thereof.

The tube network 214 couples the sampling tube's first end 220 to both the first valve 210 and the vacuum device 212. In this example, the tube network 214 includes a first tube 214a which has one end 224 coupled to the sampling tube's first end 220 and another end 226 coupled to a first end 228 of a multi-opening fitting 214b (e.g., T-shaped fitting 214b (shown), Y-shaped fitting 214b). The T-shaped fitting 214b has a second end 230 coupled to one end 232 of a second tube 214c which has another end 234 coupled to one end 235 of the vacuum device 212. The T-shaped fitting 214b also has a third end 236 coupled to one end 238 of a third tube 214d which has another end 240 coupled to one end 242 of the first valve 210. The tube network 214 also includes a fourth tube 214e which has one end 245 coupled to a second end 244 of the first valve 210 and a second end 246 which is open to the atmosphere (ambient air). The skilled person will appreciate that the tube network 214 could have many different configurations employing one or more interconnected flexible or non-flexible tubes and/or one or more fittings so long as the vacuum device 212 is coupled to the sampling tube's first end 220 without the first valve 210 being positioned there between, and the first valve 210 is coupled to the sampling tube's first end 220 without the vacuum device 212 being positioned there between.

If desired, the sampling tube 208 can have the electrical isolation sleeve 216 (e.g., ceramic sleeve 216) positioned around at least a portion thereof. The three-axis positioning stage 218 includes one or more rods 248 (two shown) extending therefrom and attached to the electrical isolation sleeve 216 on the sampling tube 208. The electrical isolation sleeve 216 functions to electrically isolate the sample tube 208 from the three-axis positioning stage 218. The three-axis positioning stage 218 operates to move the sampling tube's second end 222 into and out of the molten glass 204 to obtain the glass sample 202 from the glass melting vessel 206. In this example, the three-axis positioning stage 218 includes a support unit 250 which moves the rods 248 in a vertical direction with the aid of a motor 252. The three-axis positioning stage 218 also includes a hand crank 254 which moves at least the rods 248 and the supporting unit 250 in a horizontal direction. Alternatively, the three-axis positioning stage 218 could be attached directly to the sampling tube 208 without the presence of the electrical isolation sleeve 216. In fact, the three-axis positioning stage 218 is optional and does not need to be used but instead a person can grip and move the sampling tube 208 into and out of the molten glass 204 to obtain the glass sample 202 from the glass melting vessel 206.

The glass sampling apparatus 200 can be used in a wide-variety of ways to obtain the glass sample 202 from the molten glass 204 within the glass melting vessel 206. Two exemplary ways in which the glass sampling apparatus 200 (without the electrical isolation sleeve 216 and the three-axis positioning stage 218) can be used to obtain the glass sample 202 from the molten glass 204 within the glass melting vessel 206 will be described in detail next with respect to FIGS. 3A-3E and 4A-4G.

Referring to FIGS. 3A-3E, there are illustrated several diagrams used to explain the sequence of steps about how the glass sampling apparatus 200 is used to obtain the glass sample 202 (surface molten glass or near surface molten glass) from the molten glass 204 within the glass melting vessel 206 in accordance with an embodiment of the present invention. Beginning in step 302, the glass sampling apparatus 200 has the first valve 210 opened while the sampling tube's second end 222 is located outside of the molten glass 204 within the glass melting vessel 206 (see FIG. 3A). In step 304, the glass sampling apparatus 200 with the opened first valve 210 has the sampling tube's second end 222 inserted into the molten glass 204 within the glass melting vessel 206 (see FIG. 3B). If desired, the three-axis positioning stage 218 can be used to insert the sampling tube's second end 222 into the molten glass 204 within the glass melting vessel 206.

Figure 3B:
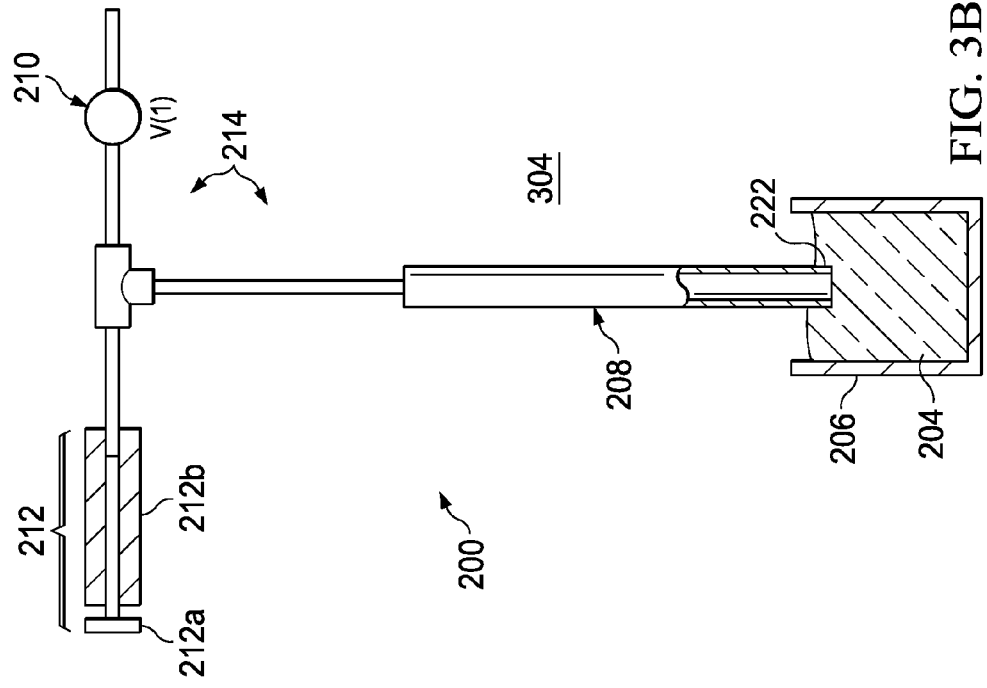
FIGS. 3A-3E are several diagrams used to explain the sequence of steps about how the glass sampling apparatus shown in FIG. 2 can be used to obtain the glass sample (surface molten glass or near surface molten glass) from the molten glass within the glass melting vessel in accordance with an embodiment of the present invention.
Figure 3A:
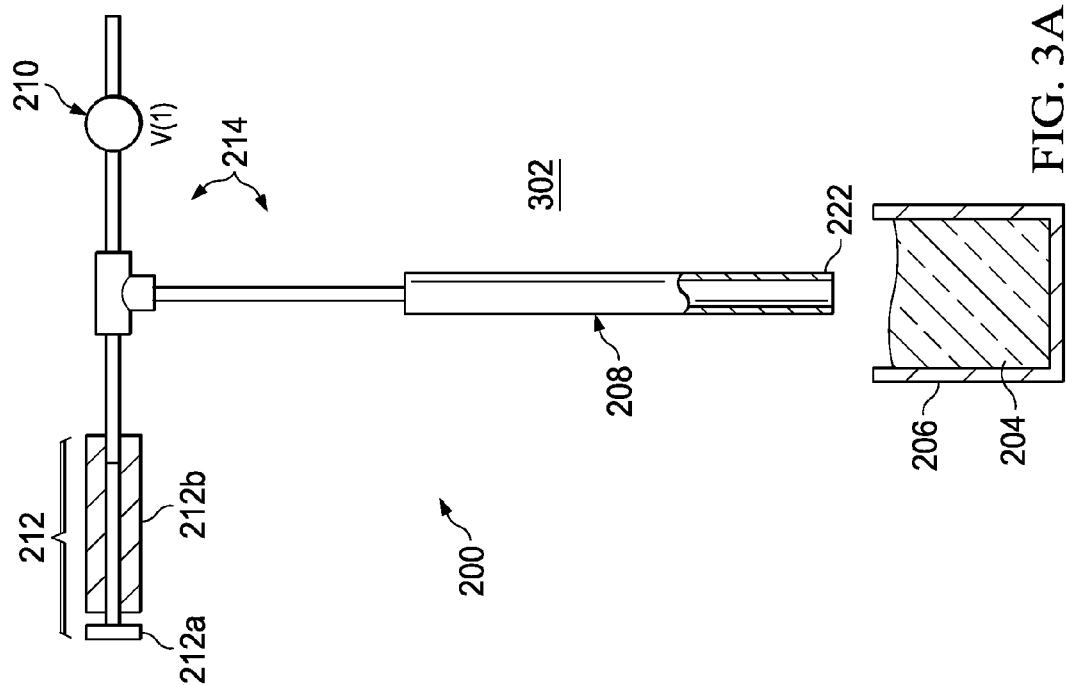
Figure 3C:
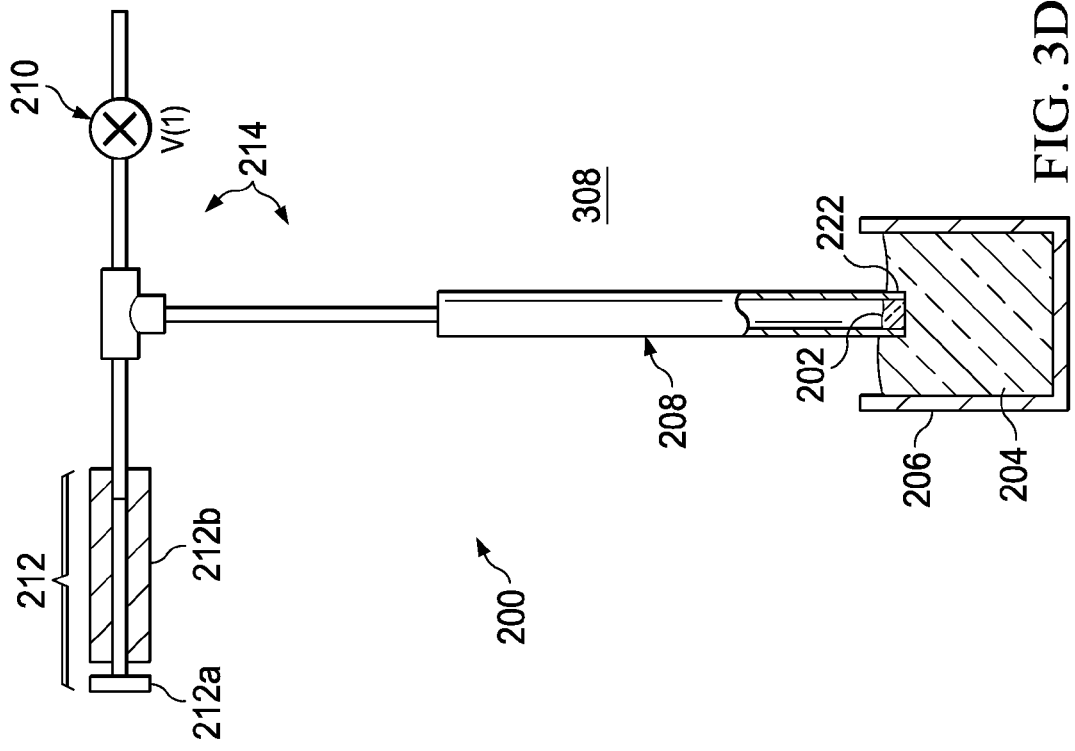

In step 306, the glass sampling apparatus 200 with the opened first valve 210 and the sampling tube's second end 222 inserted into the molten glass 204 is left in this position for a certain amount of time (e.g., one minute or more) to allow the glass sample 202 to flow-up into the sampling tube's second end 222 (see FIG. 3C). Basically, the glass sample 202 starts to flow-up into the sampling tube's second end 222 as the sampling tube 208 is lowered into the molten glass 204. The glass sample 202 inside the sampling tube's second end 222 stays at the same level as the molten glass 204 outside of the sampling tube 208. Hence, the glass sampling device 200 obtains the glass sample 202 from an area that primarily consists of surface glass and near surface glass in the sampled area of the molten glass 204.

Figure 3D:
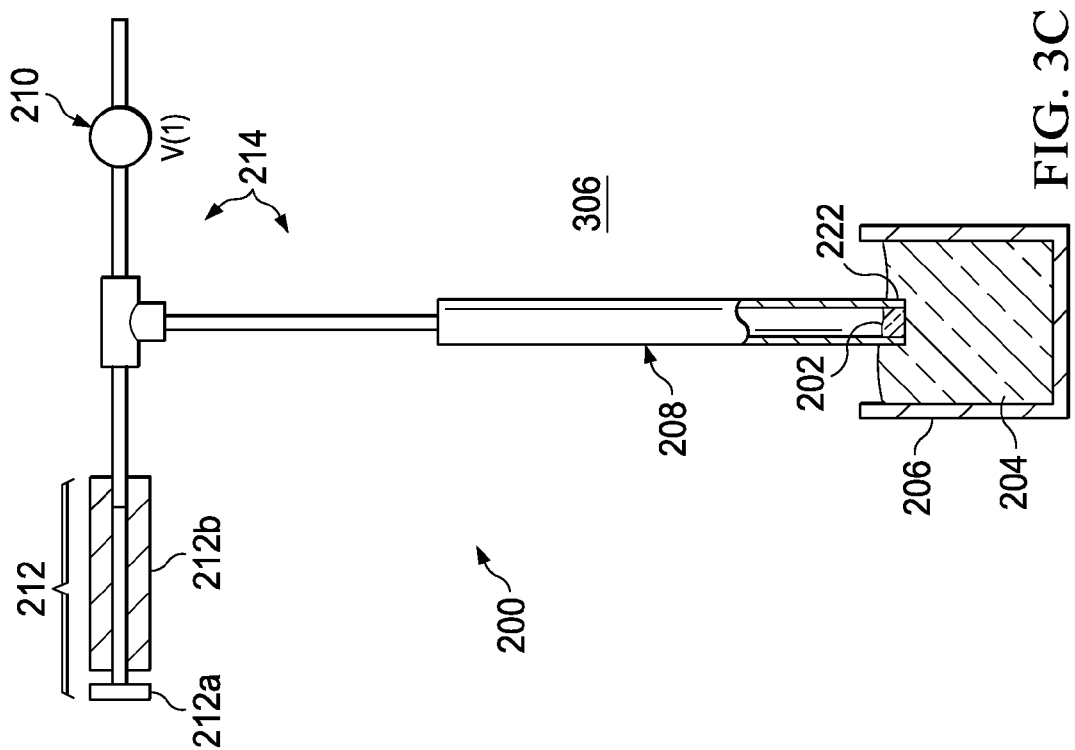
Figure 3E:
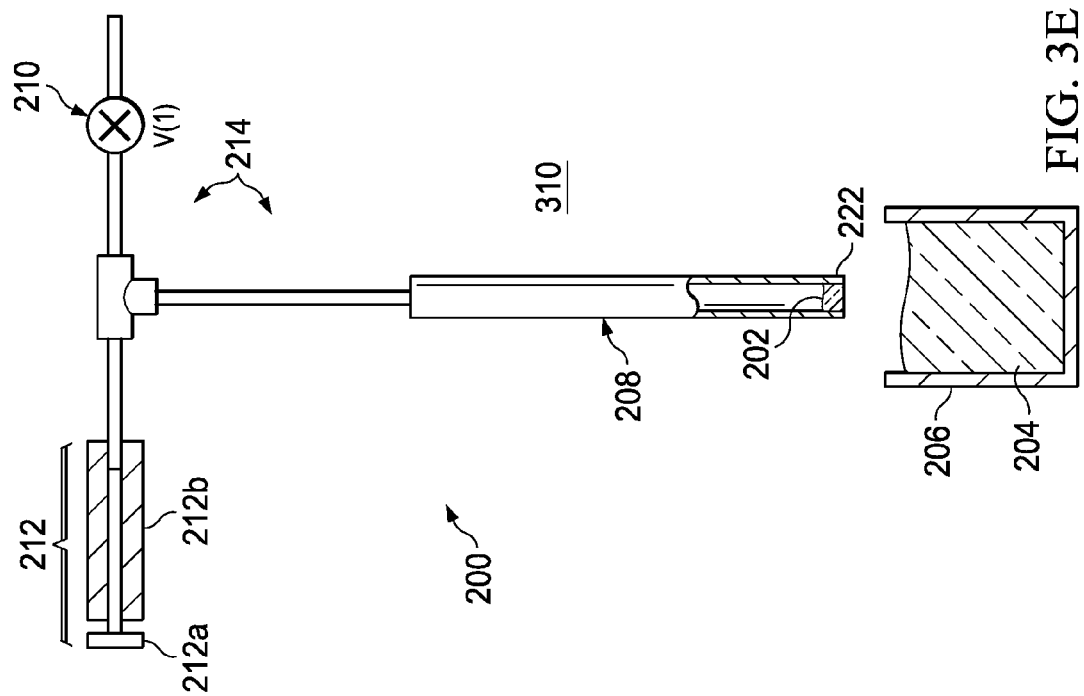

In step 308, the glass sampling apparatus 200 with the glass sample 202 located therein has the first valve 210 closed (see FIG. 3D). In step 310, the glass sampling apparatus 200 with the closed first valve 210 and the glass sample 202 located in the sampling tube's second end 222 is extracted from the molten glass 204 within the glass melting vessel 206 (see FIG. 3E). The closed first valve 210 prevents the glass sample 202 from flowing out of the sampling tube 208 while it is being pulled out of the molten glass 204 in the melting vessel 206. The vacuum device 212 does not need to be used during this sampling technique so the plunger 212a can remain fully pushed into the housing of the syringe 212b. However, if desired the plunger 212a can be partially pulled-out from the syringe 212b after step 308 to create a vacuum to help keep the glass sample 202 from flowing out of the sampling tube 208 while it is being pulled out of the molten glass 204 in the melting vessel 206.

Referring to FIGS. 4A-4G, there are illustrated several diagrams used to explain the sequence of steps about how the glass sampling apparatus 200 is used to obtain the glass sample 202 (non-surface molten glass and non-near surface molten glass) from the molten glass 204 within the glass melting vessel 206 in accordance with another embodiment of the present invention. Beginning in step 402, the glass sampling apparatus 200 has the first valve 210 closed while the sampling tube's second end 222 is located outside of the molten glass 204 within the glass melting vessel 206 (see FIG. 4A). At this point, the plunger 212a would be fully pushed into the syringe 212b. In step 404, the glass sampling apparatus 200 with the closed first valve 210 has the sampling tube's second end 222 inserted to a desired depth in the molten glass 204 within the glass melting vessel 206 (see FIG. 4B). If desired, the three-axis positioning stage 218 can be used to insert the sampling tube's second end 222 to the desired depth in the molten glass 204 within the glass melting vessel 206. In this configuration, the surface molten glass 204 or near surface molten glass 204 will not flow into the sampling tube's second end 222 because the closed first valve 210 and the sealed vacuum device 212 (i.e. plunger 212a is fully pushed into the syringe 212b) create a slight positive pressure inside the sampling tube 202 as it is lowered into the molten glass 204. This positive pressure which is due to the heating of the trapped air inside the sampling tube 202 effectively keeps the molten glass 204 from flowing-up into the sampling tube's second end 222.

Figure 4A:
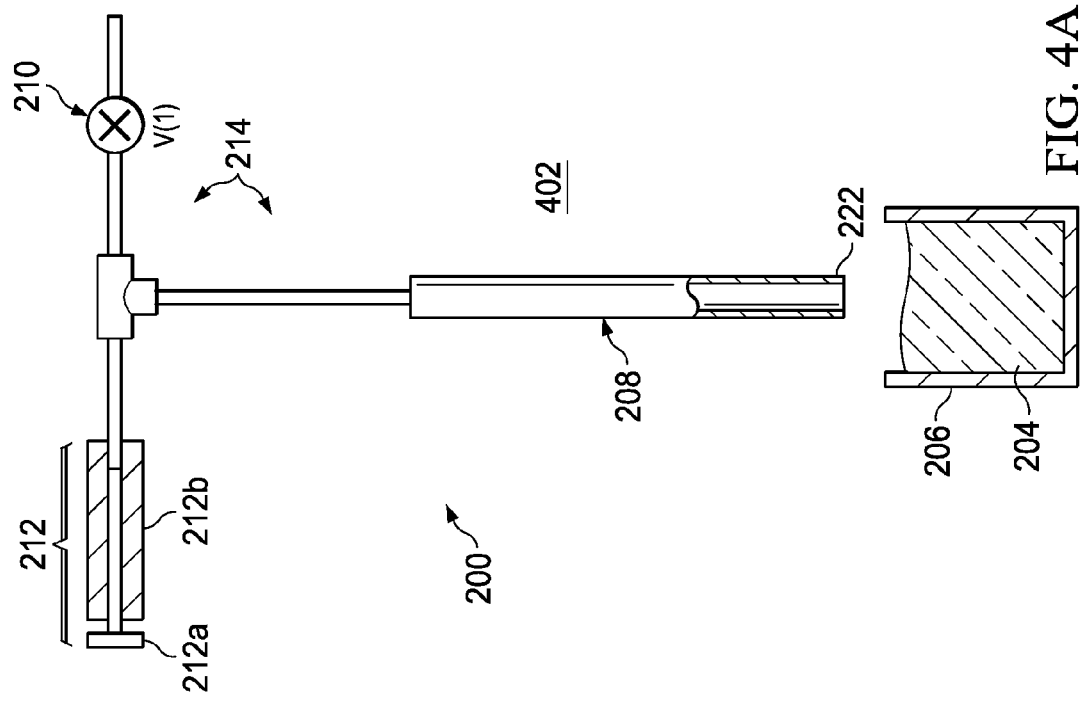
Figure 4C:
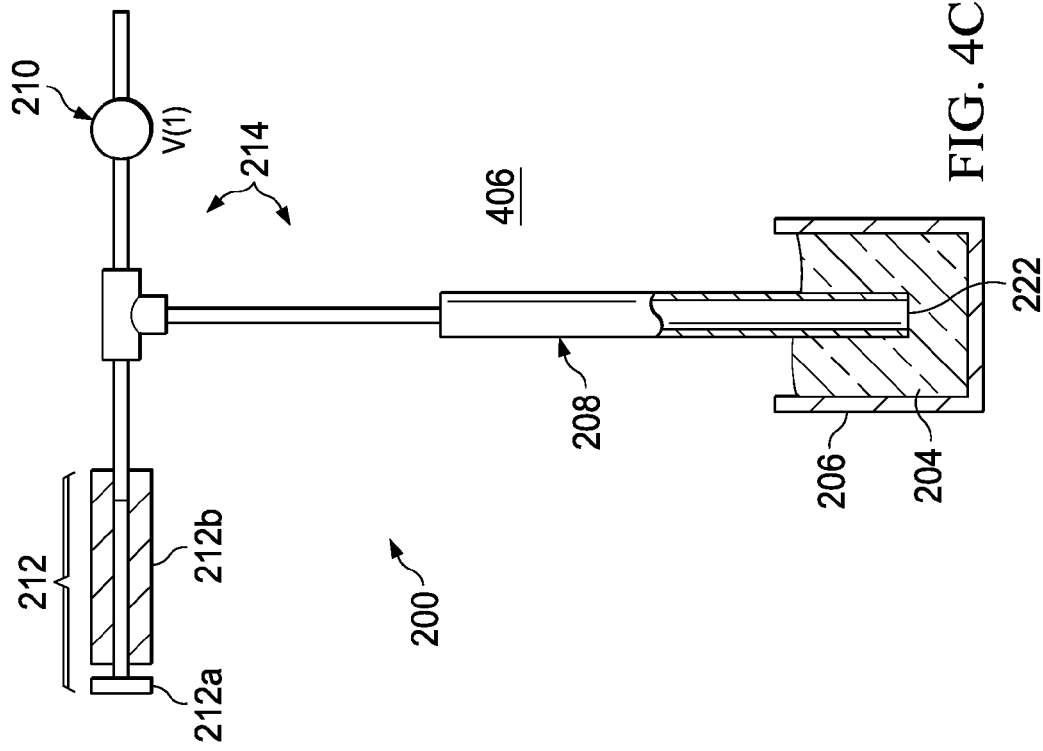
Figure 4B:
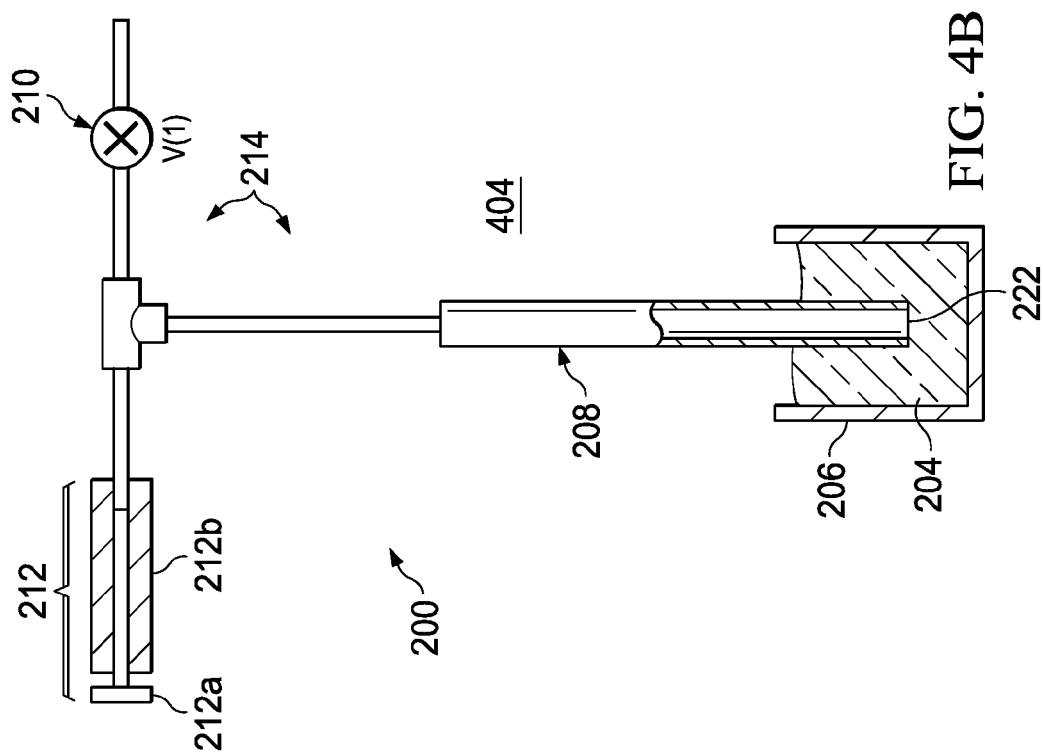

In step 406, the glass sampling apparatus 200 has the first valve 210 opened while the sampling tube's second end 222 is located at the desired depth in the molten glass 204 within the glass melting vessel 206 (see FIG. 4C). In step 408, the glass sampling apparatus 200 with the opened first valve 210 and the sampling tube's second end 222 inserted at the desired depth in the molten glass 204 is left in this position for a certain amount of time (e.g., one minute or more) to allow the glass sample 202 to flow-up into the sampling tube's second end 222 (see FIG. 4D). In this configuration, the molten glass 204 flows-up into the sampling tube's second end 222 as it seeks to match the glass level on the outside of the sampling tube's second end 222. At this point, the plunger 212a would still be fully pushed into the syringe 212b.

Figure 4E:
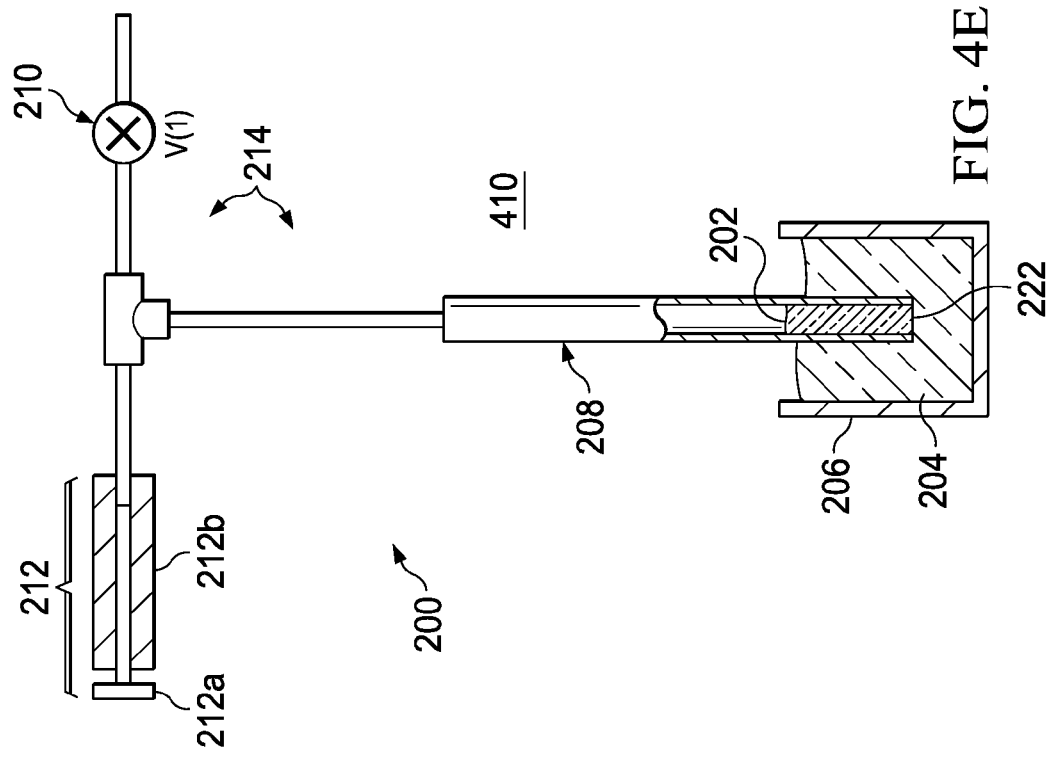
Figure 4D:
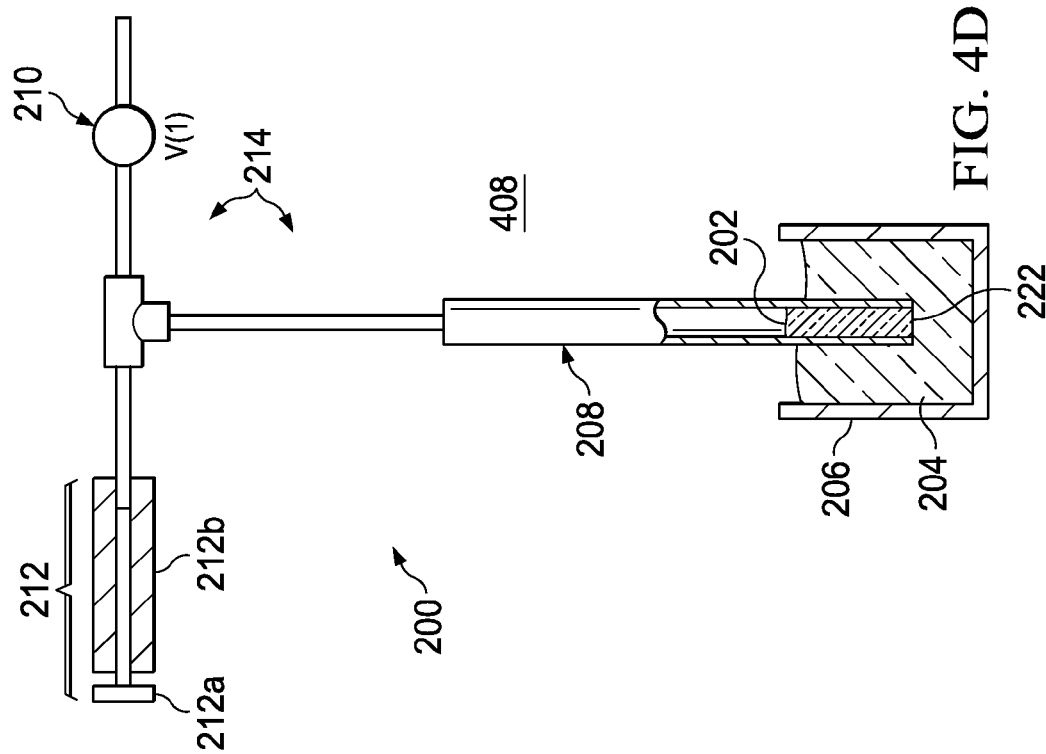

In step 410, the glass sampling apparatus 200 with the glass sample 202 located therein has the first valve 210 closed (see FIG. 4E). In step 412, the glass sampling apparatus 200 with the closed first valve 210 and the glass sample 202 located therein has the vacuum device 212 operated to create a vacuum on top of the glass sample 202 located inside the sampling tube's second end 222 (see FIG. 4F). If one wanted to sample an even larger amount of glass 204 then they could use the vacuum device 215 to create a higher vacuum during step 412. In this example, the plunger 212a would be pulled-out or slightly pulled-out from the syringe 212b to create the vacuum on top of the glass sample 202 located inside the sampling tube's second end 222. In step 414, the glass sampling apparatus 200 with the closed first valve 210 and the vacuum device 212 creating the vacuum on top of the glass sample 202 located in the sampling tube's second end 222 is extracted from the molten glass 204 within the glass melting vessel 206 (see FIG. 4G). The closed first valve 210 and the vacuum device 212 creating the vacuum on top of the glass sample 202 prevent the glass sample 202 from flowing out of the sampling tube 208 while it is being pulled out of the molten glass 204 in the melting vessel 206.

This glass sampling technique is especially helpful for sampling molten glass 204 (production molten glass 204) when there is a layer of stagnant molten glass (surface molten glass or near surface molten glass) in the glass melting vessel 206 which is not representative of the production molten glass 204. For example, in the level probe standpipe, there can be a substantial layer of stagnant molten glass above the glass that is flowing through the finer to stir chamber tube (see FIG. 8). The glass sampling apparatus 200 can be used to sample the flowing molten glass 204 by keeping all of the outlets including the first valve 210 and the vacuum device 212 closed as the sampling tube's second end 222 is lowered through the level probe standpipe into the finer to stir chamber tube. A detailed discussion about this location and some of the different locations in a glass manufacturing system where the glass sampling apparatus 200 can be used to obtain a glass sample 202 is provided below with respect to FIG. 8.

Referring to FIG. 5, there is a schematic of a glass sampling apparatus 500 configured to obtain a glass sample 502 from molten glass 504 within a glass melting vessel 506 in accordance with an embodiment of the present invention. The glass sampling apparatus 500 includes a sampling tube 508, a first valve 510 (e.g., first ball valve 510), a second valve 511 (e.g., second ball valve 511), a vacuum device 512 (e.g., plunger 512a and syringe 512b), a tube network 514 (e.g., four tubes 514a, 514c, 514d and 514e, and a T-shaped fitting 514b), an electrical isolation sleeve 516 (optional), and a three-axis positioning stage 518 (optional).

The sampling tube 508 (sampling pipe 508) has a first end 520 and a second end 522, where the second end 522 is used to obtain the glass sample 502 from the molten glass 504 within the glass melting vessel 506. The sampling tube 508 can any length depending on the location of sampling area and made from quartz, platinum, rhodium, palladium, iridium, rhenium, ruthenium, osmium, other refractory tube material, or some combination thereof.

The tube network 514 couples the sampling tube's first end 520 to both the first valve 510 and the vacuum device 512. In this example, the tube network 514 includes a first tube 514a which has one end 524 coupled to the sampling tube's first end 520 and another end 526 coupled to a first end 528 of the second valve 511 which has a second end 530 coupled to a first end 532 of a multi-opening fitting 514b (e.g., T-shaped fitting 514b (shown), Y-shaped fitting 514b) The T-shaped fitting 514b has a second end 534 coupled to one end 536 of a second tube 514c which has another end 538 coupled to a first end 539 of the vacuum device 512. The T-shaped fitting 514b also has a third end 540 coupled to one end 542 of a third tube 514d which has another end 544 coupled to one end 546 of the first valve 510. The tube network 514 also includes a fourth tube 514e which has one end 548 coupled to a second end 550 of the first valve 510 and another end 552 which is open to the atmosphere (ambient air). The skilled person will appreciate that the tube network 514 could have many different configurations employing one or more interconnected flexible and non-flexible tubes and/or one or more fittings so long that the vacuum device 512 is coupled to the sampling tube's first end 520 with the second valve 511 positioned there between and without the first valve 510 being positioned there between, and the first valve 510 is coupled to the sampling tube's first end 520 with the second valve 511 positioned there between and without the vacuum device 512 being positioned there between.

If desired, the sampling tube 508 can have the electrical isolation sleeve 516 (e.g., ceramic sleeve 516) positioned around at least a portion thereof. The three-axis positioning stage 518 which includes one or more rods 556 (two shown)

extending therefrom and attached to the electrical isolation sleeve 516 on the sampling tube 508. The electrical isolation sleeve 516 functions to electrically isolate the sample tube 508 from the three-axis positioning stage 518. The three-axis positioning stage 518 operates to move the sampling tube's second end 522 into and out of the molten glass 504 to obtain the glass sample 502 from the glass melting vessel 506. In this example, the three-axis positioning stage 518 includes a support unit 558 which moves the rods 556 in a vertical direction with the aid of a motor 560. The three-axis positioning stage 518 also includes a hand crank 562 which moves at least the rods 556 and the support unit 558 in a horizontal direction. Alternatively, the three-axis positioning stage 518 could be attached directly to the sampling tube 508 without the presence of the electrical isolation sleeve 516. In fact, the three-axis positioning stage 518 is optional and does not need to be used but instead a person can grip and move the sampling tube 508 into and out of the molten glass 504 to obtain the glass sample 502 from the glass melting vessel 506.

The glass sampling apparatus 500 can be used in a wide-variety of ways to obtain the glass sample 502 from the molten glass 504 within the glass melting vessel 506. Two exemplary ways in which the glass sampling apparatus 500 (without the electrical isolation sleeve 516 and the three-axis positioning stage 518) can be used to obtain the glass sample 502 from the molten glass 504 within the glass melting vessel 506 will be described in detail next with respect to FIGS. 6A-6E and 7A-7G.

Referring to FIGS. 6A-6E, there are illustrated several diagrams used to explain the sequence of steps about how the glass sampling apparatus 500 is used to obtain the glass sample 502 (surface molten glass or near surface molten glass) from the molten glass 504 within the glass melting vessel 506 in accordance with an embodiment of the present invention. Beginning in step 602, the glass sampling apparatus 500 has the first valve 510 and second valve 511 opened while the sampling tube's second end 522 is located outside of the molten glass 504 within the glass melting vessel 506 (see FIG. 6A). In step 604, the glass sampling apparatus 500 with the opened first valve 510 and the opened second valve 511 has the sampling tube's second end 522 inserted into the molten glass 504 within the glass melting vessel 506 (see FIG. 6B). If desired, the three-axis positioning stage 518 can be used to insert the sampling tube's second end 522 into the molten glass 504 within the glass melting vessel 506.

In step 606, the glass sampling apparatus 500 with the opened first valve 510, the opened second valve 511, and the sampling tube's second end 522 inserted into the molten glass 504 is left in this position for a certain amount of time (e.g., one minute or more) to allow the glass sample 502 to flow-up into the sampling tube's second end 522 (see FIG. 3C). Basically, the glass sample 502 starts to flow-up into the sampling tube's second end 522 as the sampling tube 508 is lowered into the molten glass 504. The glass sample 502 inside the sampling tube's second end 522 stays at the same level as the molten glass 504 outside of the sampling tube 508. Hence, the glass sampling device 500 obtains the glass sample 502 from an area that primarily consists of surface glass and near surface glass in the sampled area of the molten glass 504.

Figure 6A:
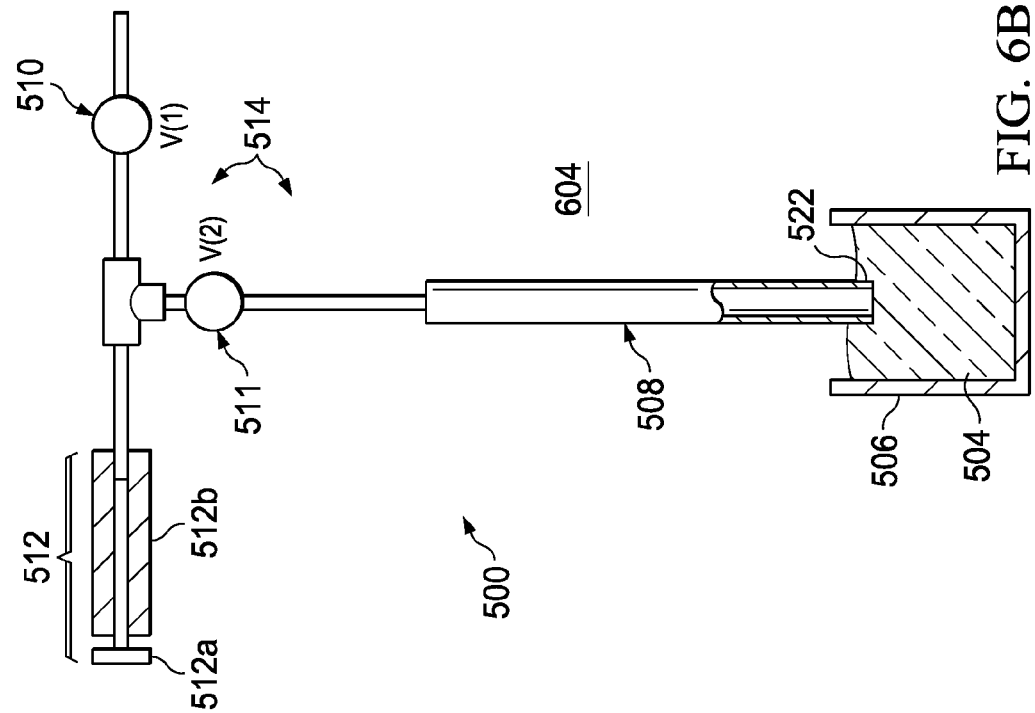
FIGS. 6A-6E are several diagrams used to explain the sequence of steps about how the glass sampling apparatus shown in FIG. 5 can be used to obtain the glass sample (surface molten glass or near surface molten glass) from the molten glass within the glass melting vessel in accordance with an embodiment of the present invention.
Figure 6B:
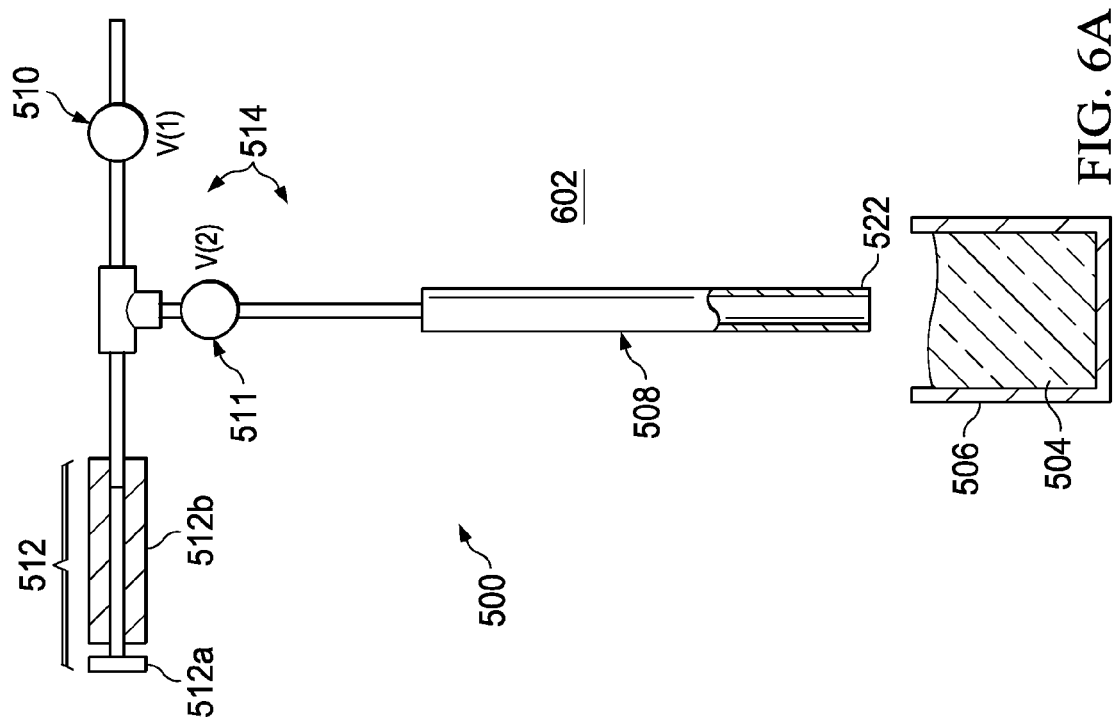
Figure 6C:
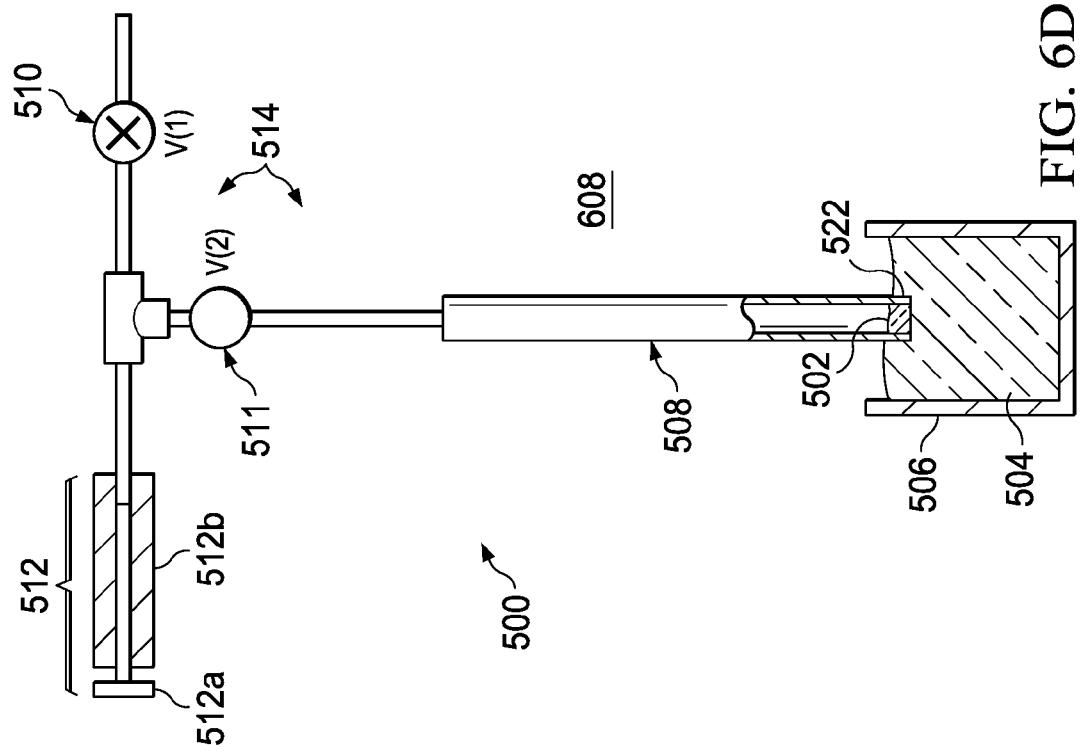
Figure 6D:
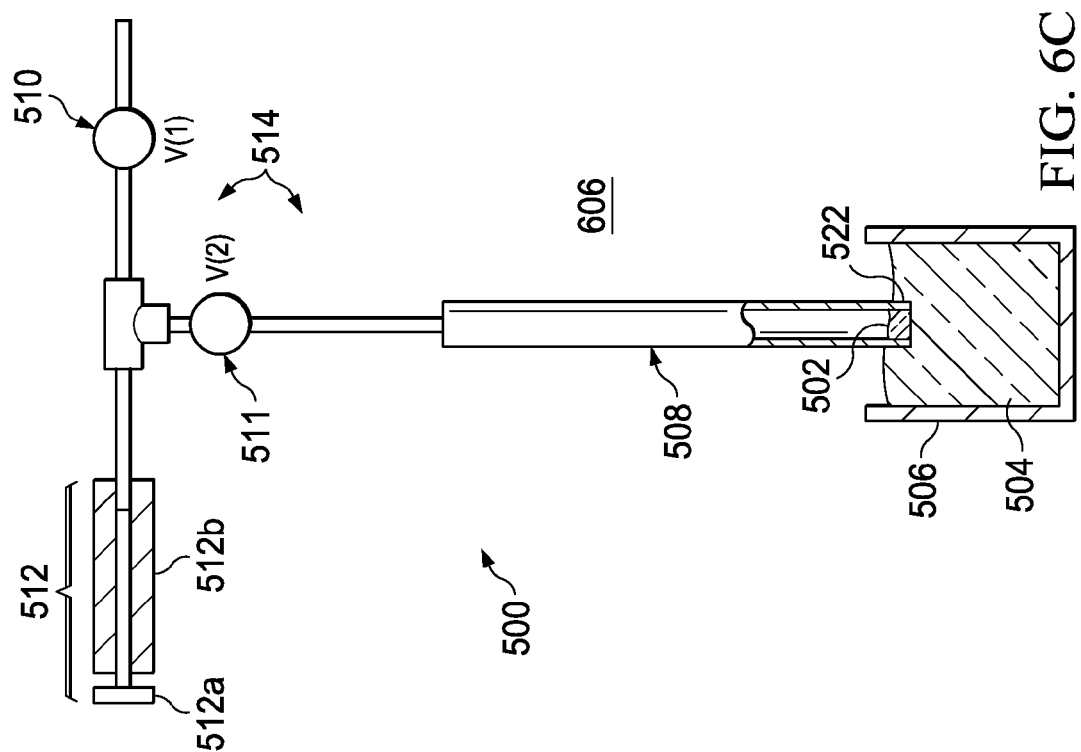
Figure 6E:
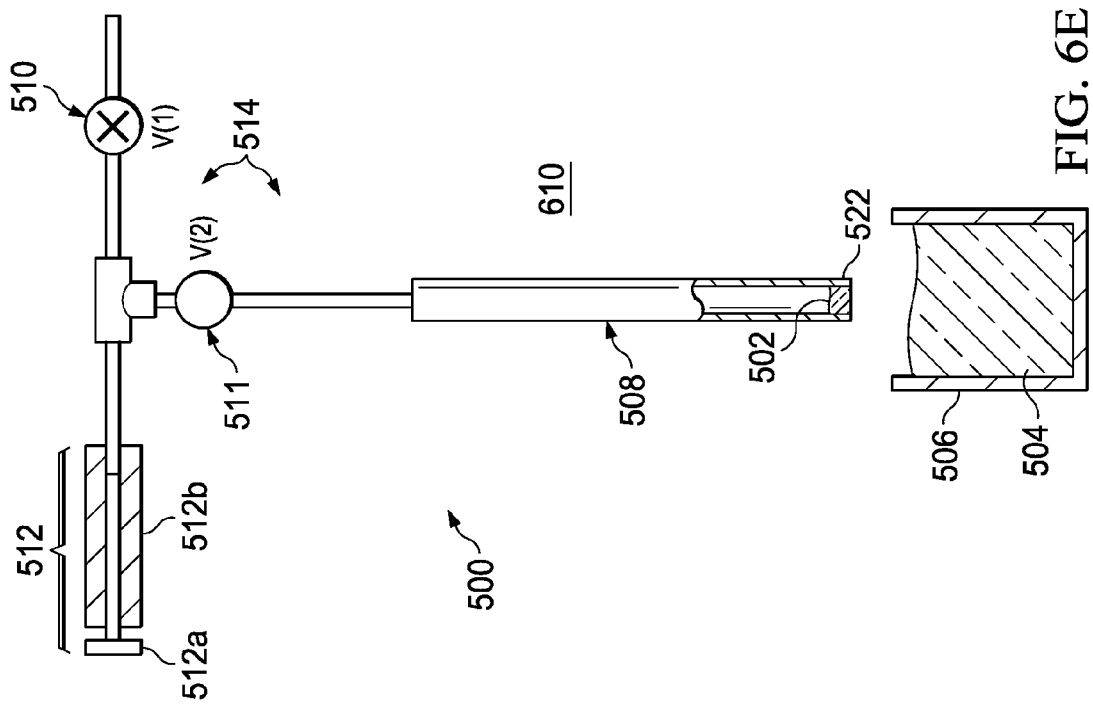

In step 608, the glass sampling apparatus 500 with the glass sample 502 located therein has at least one of the first valve 510 and the second valve 511 closed (see FIG. 6D—where the first valve 510 is closed). In step 610, the glass sampling apparatus 500 with the at least one the first valve 510 and second valve 511 closed and the glass sample 502 located in the sampling tube's second end 522 is extracted from the molten glass 504 within the glass melting vessel 506 (see FIG. 6E—where the first valve 510 is closed). The closed first valve 510 (and/or the closed second valve 511) prevents the glass sample 502 from flowing out of the sampling tube 508 while it is being pulled out of the molten glass 504 in the melting vessel 506. The vacuum device 512 does not need to be used during this sampling technique so the plunger 512a can remain fully pushed into the housing of the syringe 512b. However, if desired the plunger 512a can be partially pulled-out from the syringe 512b after step 608 assuming the second valve 511 is opened to create some additional vacuum level to help keep the glass sample 502 from flowing out of the sampling tube 508 while it is being pulled out of the molten glass 504 in the melting vessel 506.

Referring to FIGS. 7A-7G, there are illustrated several diagrams used to explain the sequence of steps about how the glass sampling apparatus 500 is used to obtain the glass sample 502 (non-surface molten glass and non-near surface molten glass) from the molten glass 504 within the glass melting vessel 506 in accordance with another embodiment of the present invention. Beginning in step 702, the glass sampling apparatus 500 has the first valve 510 and second valve 511 closed while the sampling tube's second end 522 is located outside of the molten glass 504 within the glass melting vessel 506 (see FIG. 7A). At this point, the plunger 512a would be fully pushed into the syringe 512b. In step 704, the glass sampling apparatus 500 with the closed first and second valves 510 and 511 has the sampling tube's second end 522 inserted to a desired depth in the molten glass 504 within the glass melting vessel 506 (see FIG. 7B). If desired, the three-axis positioning stage 518 can be used to insert the sampling tube's second end 522 to the desired depth in the molten glass 504 within the glass melting vessel 506. In this configuration, the surface molten glass 504 or near surface molten glass 504 will not flow into the sampling tube's second end 522 because the closed first and second valves 510 and 511 create a slight positive pressure inside the sampling tube 502 as it is lowered into the molten glass 504. This positive pressure which is due to the heating of the trapped air inside the sampling tube 502 effectively keeps the molten glass 104 from flowing-up into the sampling tube's second end 522.

Figure 7A:
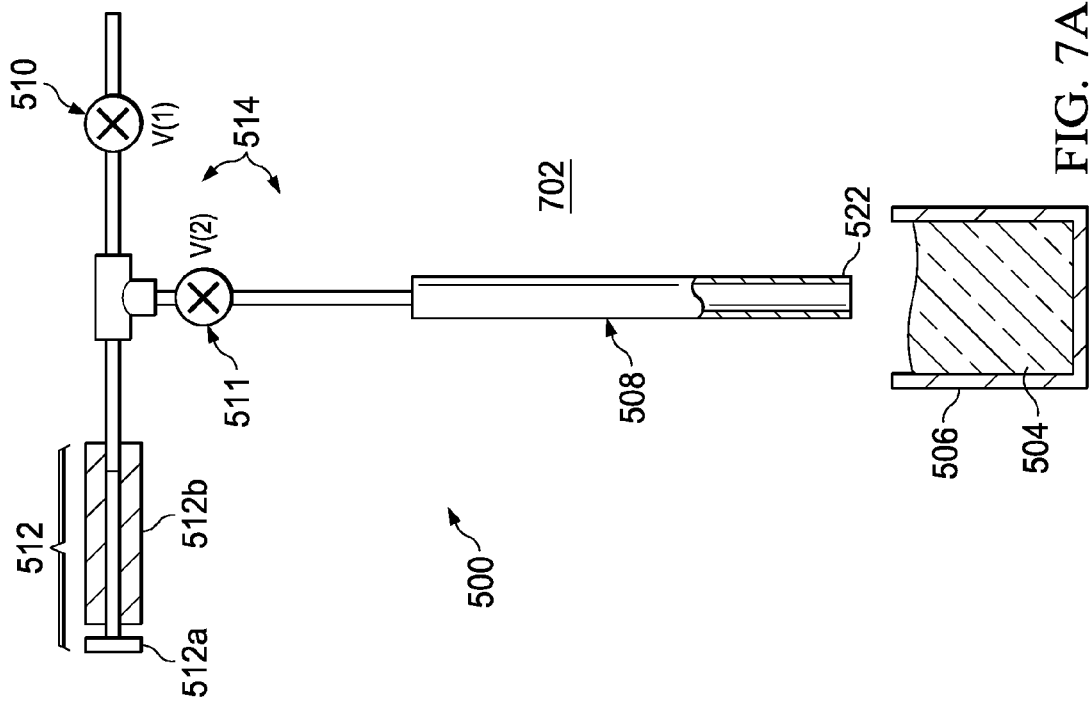
FIGS. 7A-7G are several diagrams used to explain the sequence of steps about how the glass sampling apparatus shown in FIG. 5 can be used to obtain the glass sample (non-surface molten glass and non-near surface molten glass)
Figure 7C:
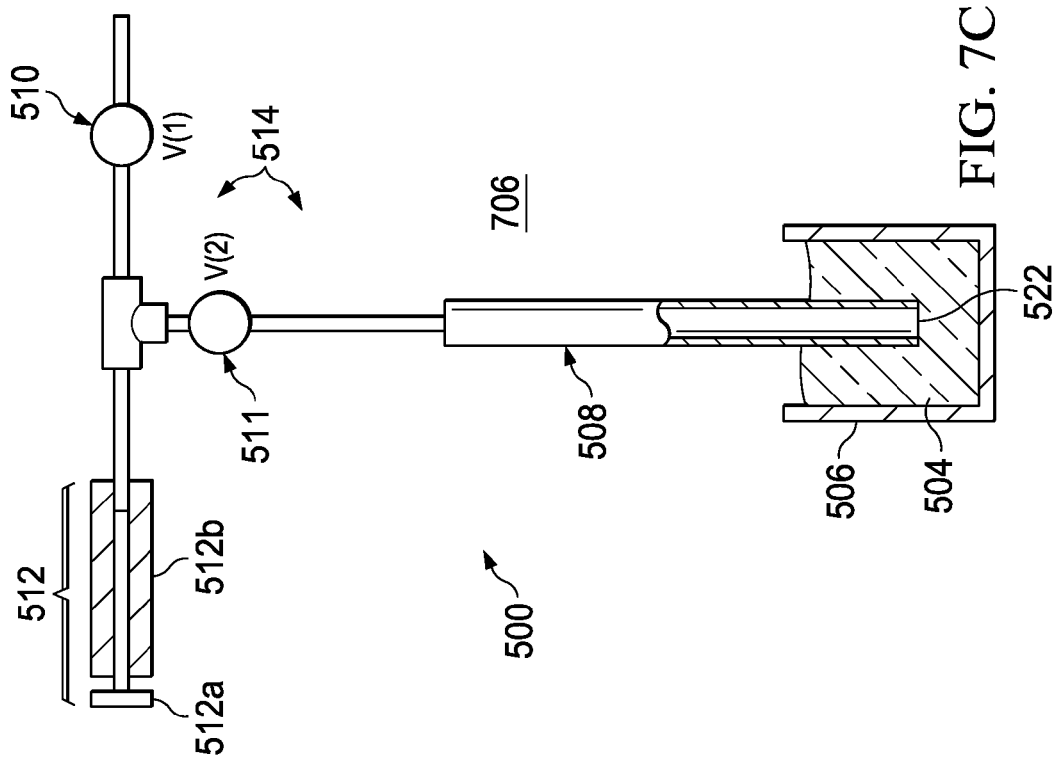
Figure 7B:
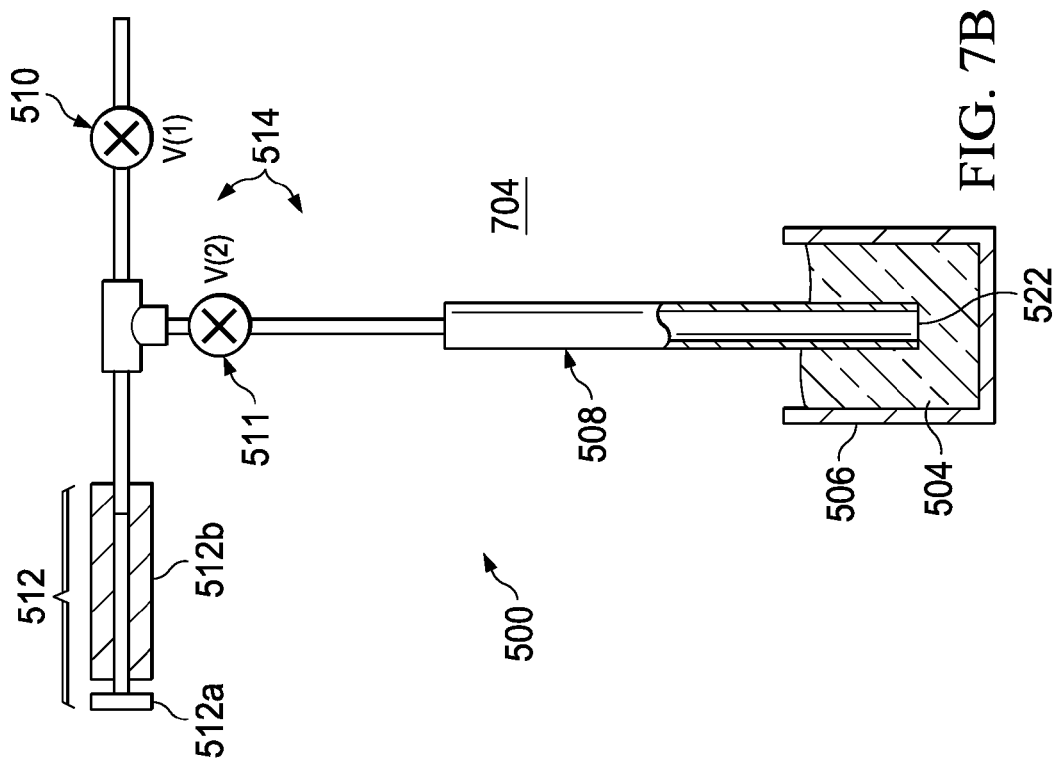
Figure 7D:
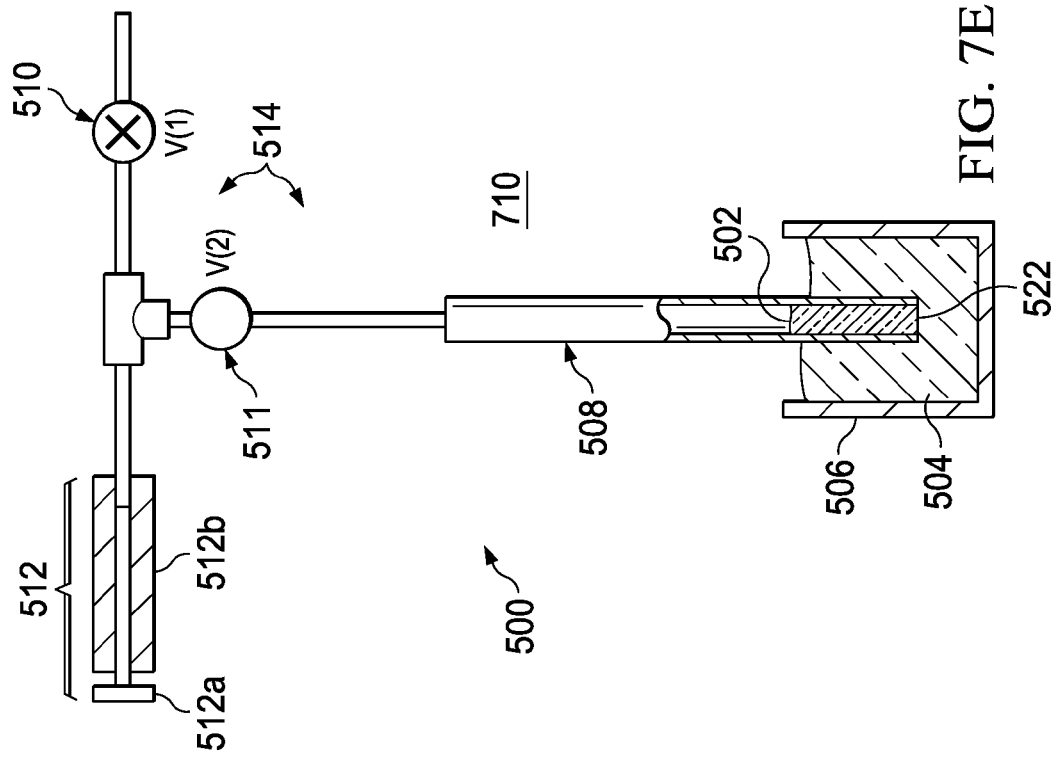

In step 706, the glass sampling apparatus 500 has the first and second valves 510 and 511 opened while the sampling tube's second end 522 is located at the desired depth in the molten glass 504 within the glass melting vessel 506 (see FIG. 7C). In step 708, the glass sampling apparatus 500 with the opened first and second valves 510 and 511 and the sampling tube's second end 522 inserted at the desired depth in the molten glass 504 is left in this position for a certain amount of time (e.g., one minute or more) to allow the glass sample 502 to flow-up into the sampling tube's second end 522 (see FIG. 7D). In this configuration, the molten glass 504 flows-up into the sampling tube's second end 522 as it seeks to match the glass level on the outside of the sampling tube's second end 522. At this point, the plunger 512a would still be fully pushed into the syringe 512b.

Figure 7E:
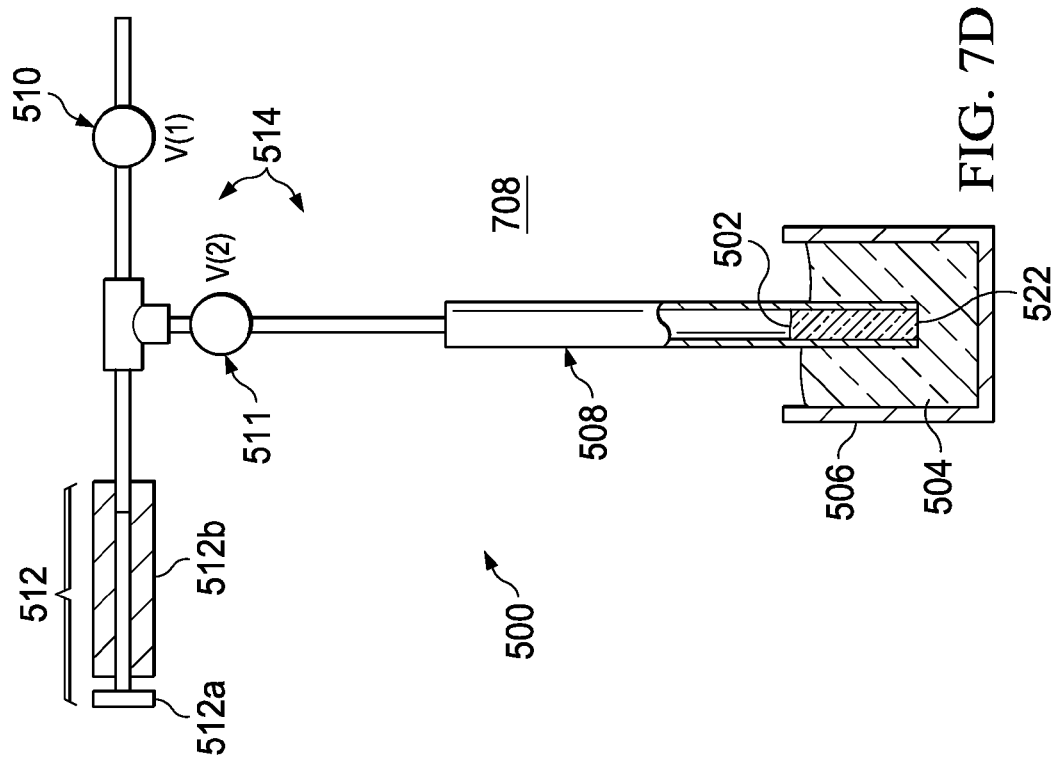
Figure 7G:
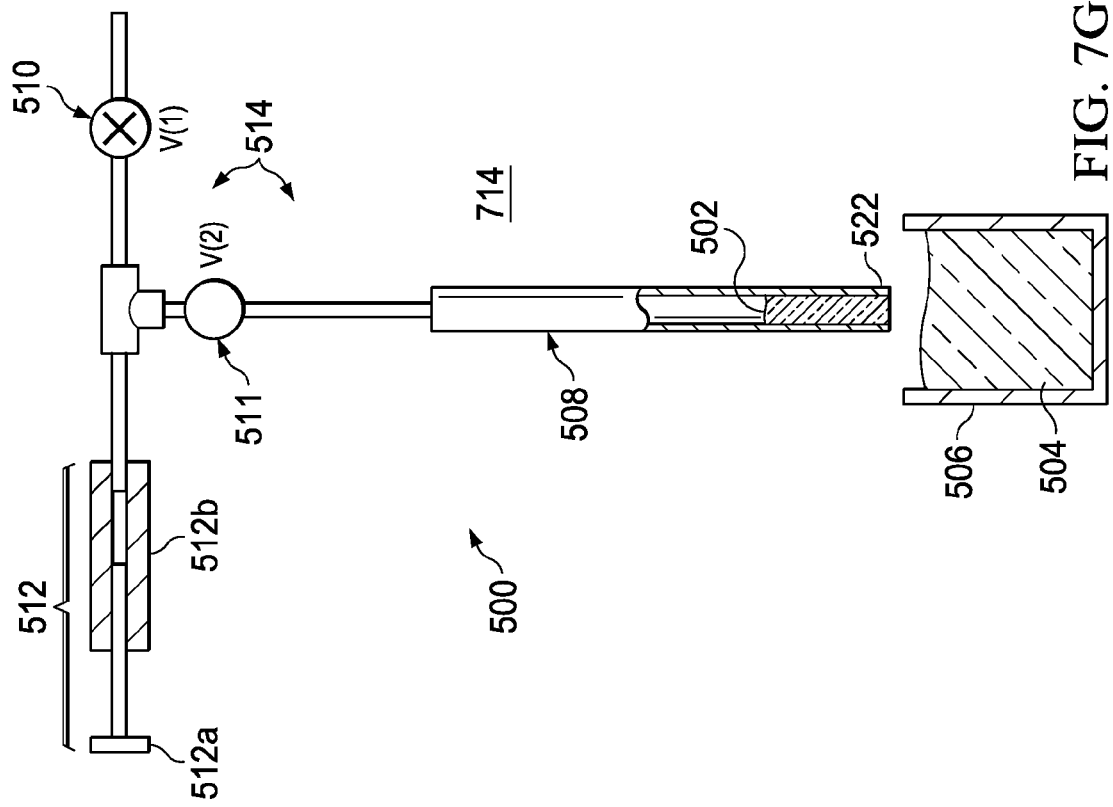
Figure 7F:
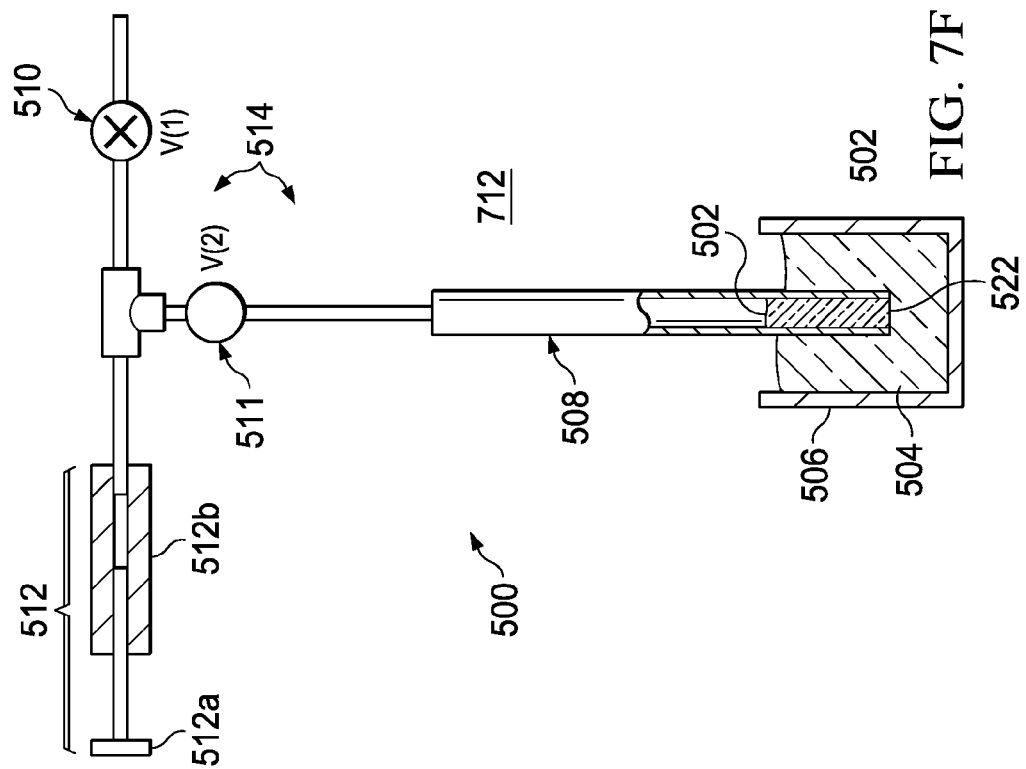

In step 710, the glass sampling apparatus 500 with the glass sample 502 located therein has the first valve 510 closed (see FIG. 7E). In step 712, the glass sampling apparatus 500 with the closed first valve 510, the opened second valve 511, and the glass sample 502 located therein has the vacuum device 512 operated to create a vacuum on top of the glass sample 502 located inside the sampling tube's second end 522 (see FIG. 7F). If one wanted to sample an even larger amount of glass 504 then they could use the vacuum device 512 to create a higher vacuum during step 712. In this example, the plunger 512a would be pulled-out or slightly pulled-out from the syringe 512b to create the vacuum on top of the glass sample 502 located inside the sampling tube's second end 522. In step 714, the glass sampling apparatus 500 with the closed first valve 510, the opened second valve 511, and the vacuum device 512 creating the vacuum on top of the glass sample 502 located in the sampling tube's second end 522 is extracted from the molten glass 504 within the glass melting vessel 506 (see FIG. 7G). The closed first valve 510, the opened second valve 511, and the vacuum device 512 creating the vacuum on top of the glass sample 502 prevent the glass sample 502 from flowing out of the sampling tube 508 while it is being pulled out of the molten glass 504 in the melting vessel 506.

This glass sampling technique is especially helpful for sampling molten glass 504 (production molten glass 504) when there is a layer of stagnant molten glass (surface molten glass or near surface molten glass) in the glass melting vessel 506 which is not representative of the production molten glass 504. For example, in the level probe standpipe, there is a substantial layer of stagnant molten glass above the glass that is flowing through the finer to stir chamber tube (see FIG. 8). The glass sampling apparatus 500 can be used to sample the flowing molten glass 504 by keeping all of the outlets including the first valve 510 and the vacuum device 512 closed as the sampling tube's second end 522 is lowered through the level probe standpipe into the finer to stir chamber tube. A detailed discussion about this location and some of the different locations in a glass manufacturing system where the glass sampling apparatus 500 can be used to obtain a glass sample 502 is provided below with respect to FIG. 8.

Referring to FIG. 8, there is shown a schematic view of an exemplary glass manufacturing system 800 which has several glass melting vessels from which the glass sampling apparatus 200 and 500 can be used to obtain a glass sample 202 and 502 in accordance with an embodiment of the present invention. The glass manufacturing system 800 includes a melting vessel 810, a melting-to-fining tube 815, a fining vessel 820, a finer to stir chamber tube 825 (with a level probe standpipe 827 extending therefrom), a stir chamber 830 (e.g., mixing vessel 830), a stir chamber to bowl connecting tube 835, a bowl 840 (e.g., delivery vessel 840), a downcomer 845, a fusion draw machine (FDM) 850 (which includes an inlet 855, a forming apparatus 860, and a pull roll assembly 865), and a traveling anvil machine (TAM) 870.

The melting vessel 810 is where glass batch materials are introduced as shown by arrow 812 and melted to form molten glass 814. The fining vessel 820 (e.g., finer tube 820) is connected to the melting vessel 810 by the melting-to-fining tube 815. The fining vessel 820 has a high temperature processing area that receives the molten glass 814 (not shown at this point) from the melting vessel 810 and in which bubbles are removed from the molten glass 814. The fining vessel 820 is connected to the stir chamber 830 by the finer to stir chamber connecting tube 825. The stir chamber 830 is connected to the bowl 840 by the stir chamber to bowl connecting tube 835. The bowl 840 delivers the molten glass 814 (not shown) through the downcomer 845 into the FDM 850.

The FDM 850 includes the inlet 855, the forming vessel 860 (e.g., isopipe 860), and the pull roll assembly 865. The inlet 855 receives the molten glass 814 (not shown) from the downcomer 845 and then flows to the forming vessel 860. The forming vessel 860 includes an opening 862 that receives the molten glass 814 (not shown) which flows into a trough 864 and then overflows and runs down two opposing sides 866a and 866b before fusing together at a root 868 to form the glass sheet 809. The pull roll assembly 865 receives the glass sheet 809 and outputs a drawn glass sheet 811. The TAM 870 receives the drawn glass sheet 811 and separates the drawn glass sheet 811 into separate glass sheets 813.

In this example, the glass sampling apparatus 200 and 500 can be used to obtain a glass sample 202 and 502 from several locations in the glass manufacturing system 800 including the glass melting vessel 810 (see arrow 880 through opening 811 and arrow 882 through opening 822), the level probe standpipe 827 or finer to stir chamber tube 825 (see arrow 824), the stir chamber 830 (see arrow 826), the bowl 840 (see arrow 828), and the inlet area between the downcomer 845 and the inlet 855 (see arrow 829). An exemplary glass sampling apparatus 500 being used to obtain a glass sample 502 from a research scale level probe standpipe 827 is discussed next with respect to FIGS. 9A-9G.

Figure 9A:
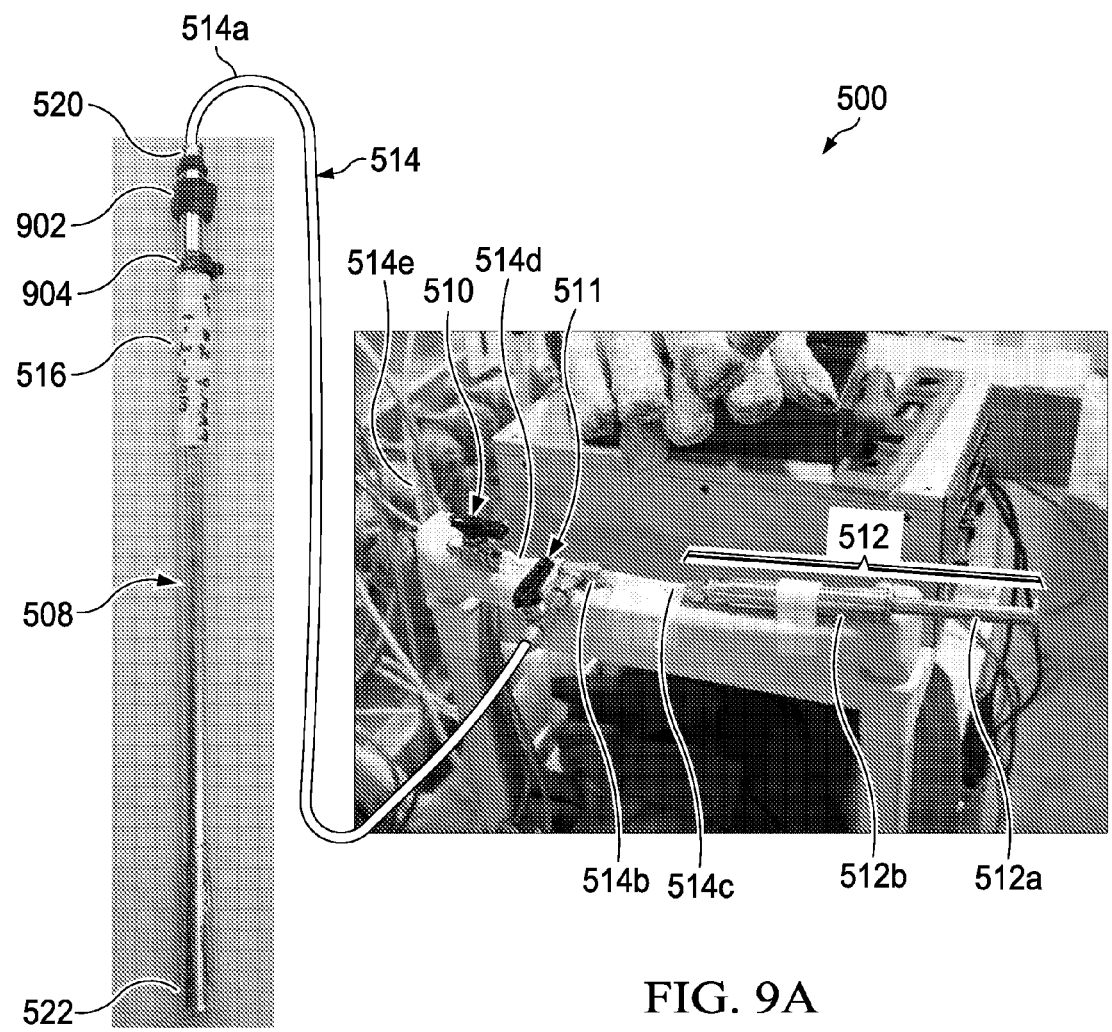

Referring to FIGS. 9A-9G, there are several photos of an exemplary glass sampling apparatus 500 being used to obtain a glass sample 502 from a research scale level probe standpipe 827 in accordance with an embodiment of the present invention. In FIG. 9A, there is a photo of the exemplary glass sampling apparatus 500 which includes the sampling tube 508, the first valve 510 (e.g., first ball valve 510), the second valve 511 (e.g., second ball valve 511), the vacuum device 512 (e.g., plunger 512a and syringe 512b), the tube network 514 (e.g., four tubes 514a, 514c, 514d and 514e, and the T-shaped fitting 514b), and the electrical isolation sleeve 516. In this example, the first tube 514a is connected to the sampling tube's first end 520 by using a Swagelok connection 902. A hose clamp 904 is placed above the electrical isolation sleeve 516 to adjust the sleeve's height on the sampling tube 508.

Figure 9B:
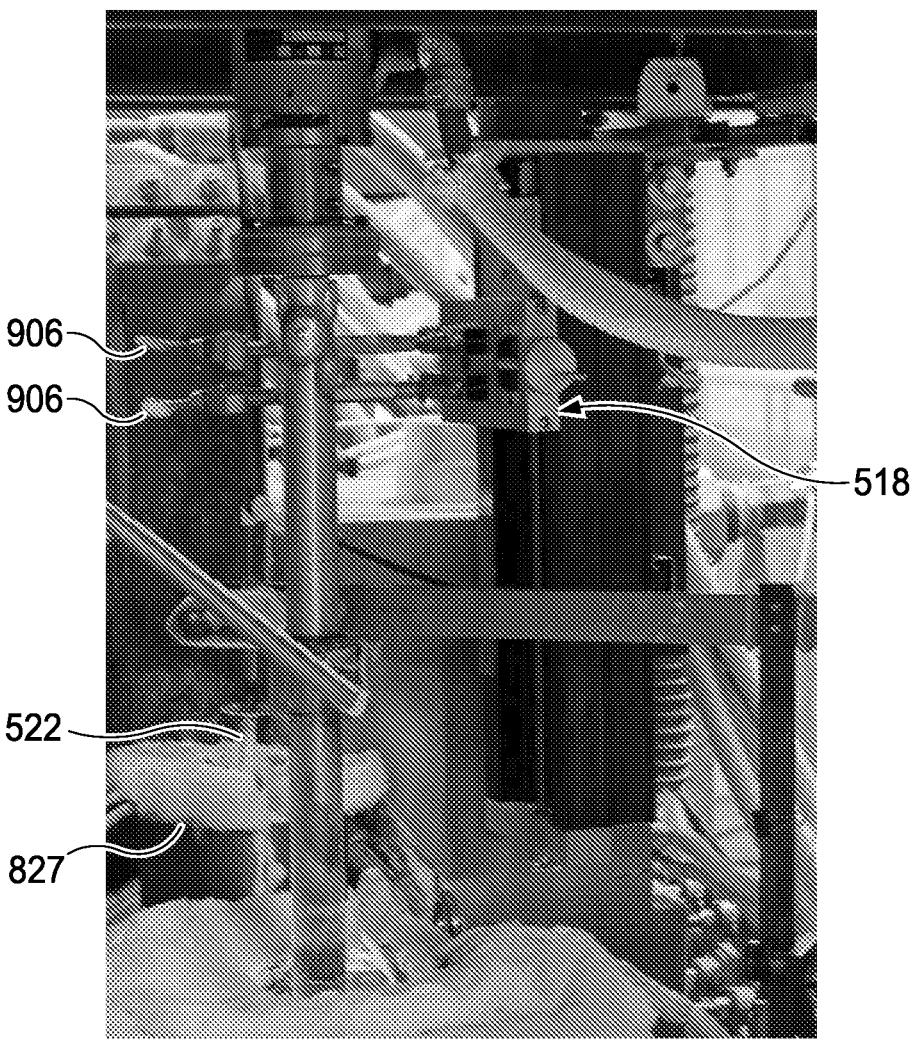

In FIG. 9B, there is a photo of the three-axis positioning stage 518 which is used to place the sampling tube's second end 522 inside the research scale level probe standpipe 827. The exemplary three-axis positioning stage 518 is configured such that the vertical position and speed are controlled by a motor 560 (not shown) while the horizontal positions are controlled by a manual stage 562 and the in/out position is controlled by manually rotating a pair of clamps 906. The 3-axis positioning stage 518 could also work for glass sampling in the bowl 840. However, glass sampling in the stir chamber 830 may not require precise 3-axis positioning thus the sampling can probably be performed by manually dipping the sampling tube 508 or by using a precise vertical positioning of the sampling tube 508.

Figure 9C:
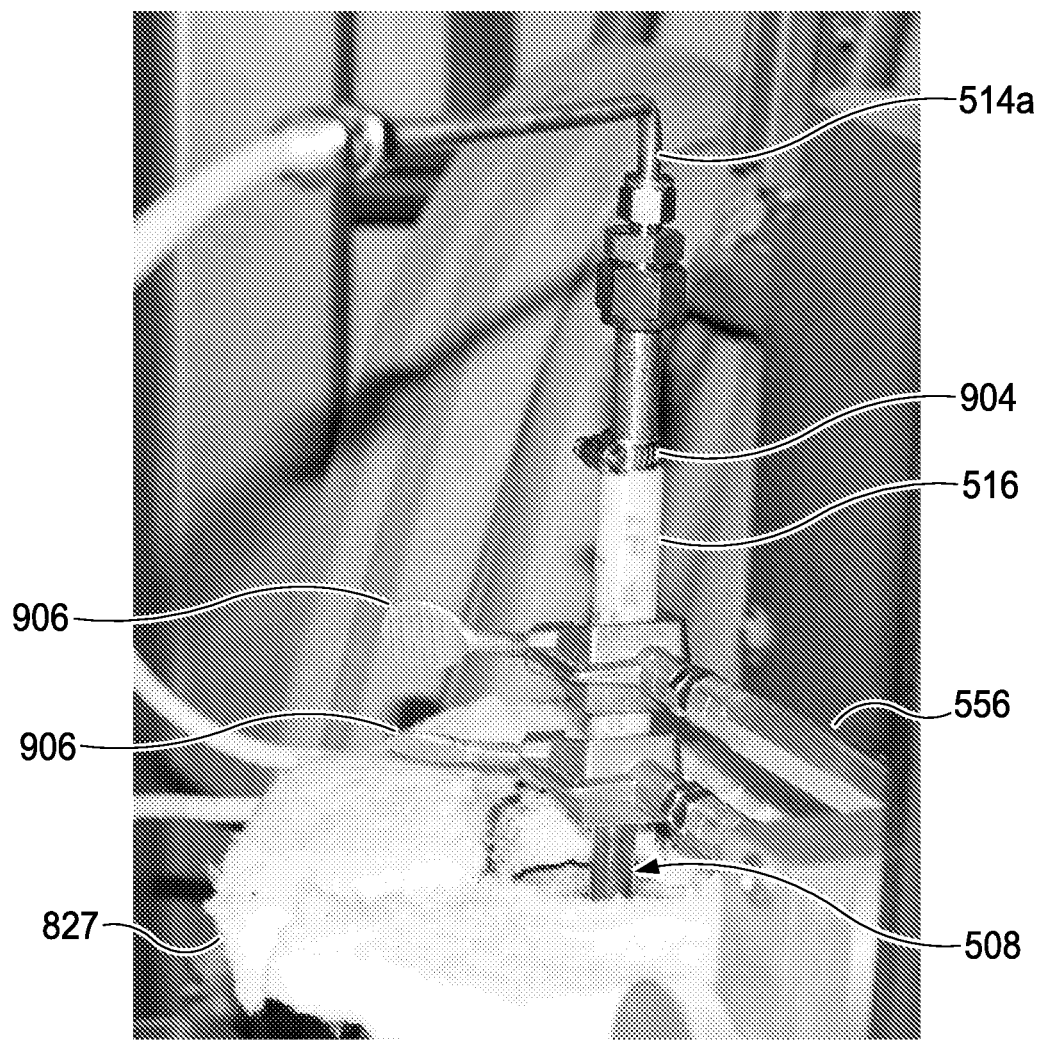

In FIG. 9C, there is a photo showing the sampling tube 508 being inserted into the research scale level probe standpipe 827 (located under insulation). In this example, the 3-axis positioning stage 518 was mounted on a frame above the research scale level probe standpipe 827 and then the sampling tube 508 (platinum sampling tube 508) was connected to the positioning stage via two rods 556 with adjustable clamps 906 attached to the terminus. The clamps 906 were connected to the electrical isolation sleeve 516 (ceramic sleeve 516) so that the 3-axis positioning system 518 was electrically isolated from the sampling tube 508. The hose clamp 904 was then placed above the electrical isolation sleeve 516 to adjust the vertical position of the sampling tube 508 with respect to the 3-axis positioning stage 518. Basically, the 3-axis positioning stage 518 was used to center and plumb the sampling tube 508 with respect to the research scale level probe standpipe 827.

Figure 9E:
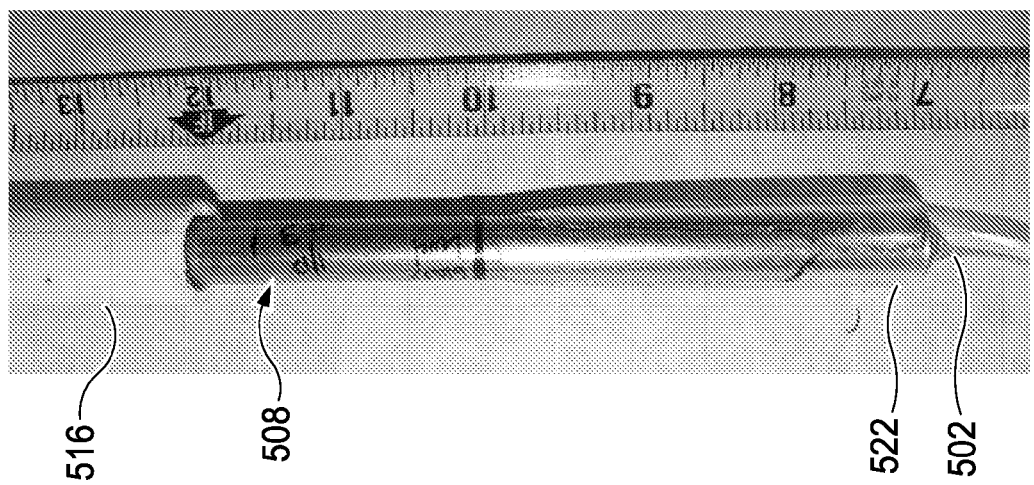
Figure 9D:
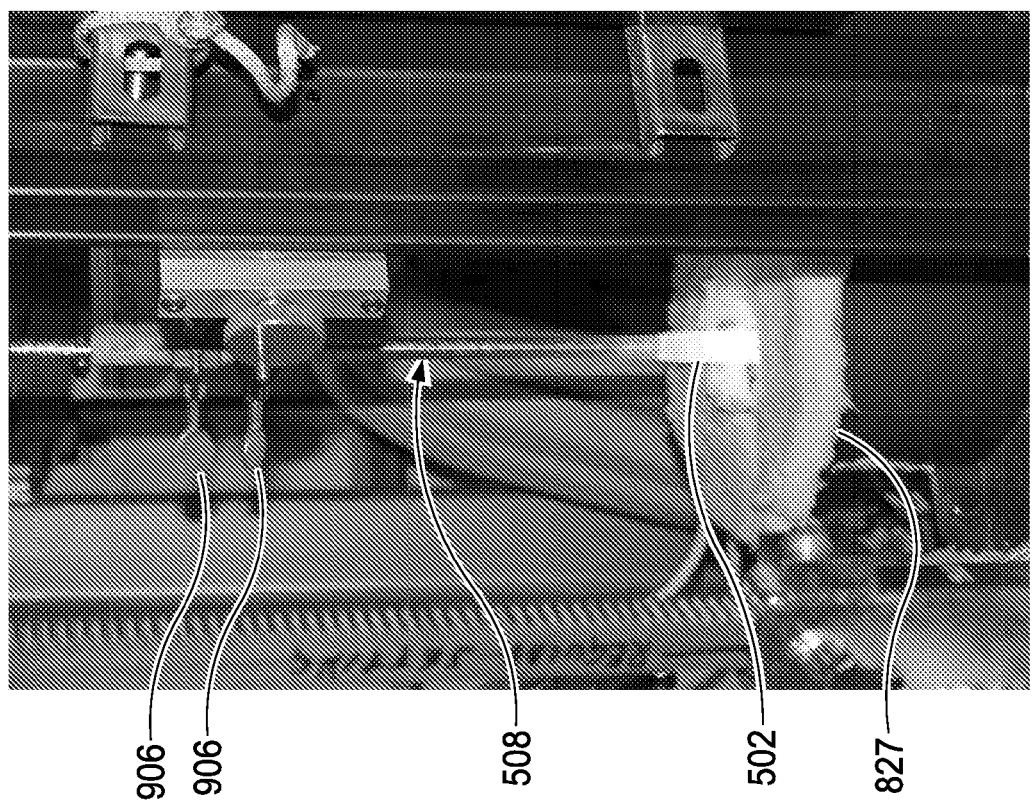

In FIG. 9D, there is a photo of the sampling tube 508 with the glass sample 502 being removed from the research scale level probe standpipe 827. In this experiment, the sampling tube 502 was inserted deep into the research scale level probe standpipe 827 and the glass sample 502 was obtained per steps 702, 704, 706, 708, 710, 712, and 714. The sampling tube 508 was removed rapidly from the molten glass 504 in the research scale level probe standpipe 827 to allow the glass sample 508 to cool and quickly solidify. Then, the sampling tube 508 was wrapped with insulation, the fittings were removed, and the sampling tube 508 containing the glass sample 502 was placed in a furnace for several hours to anneal the glass sample 502 (see FIG. 9E). Experiments have showed that a decent quality glass sample 508 could also be obtained without annealing the glass sample 508 (see FIG. 9F).

Figure 9F:
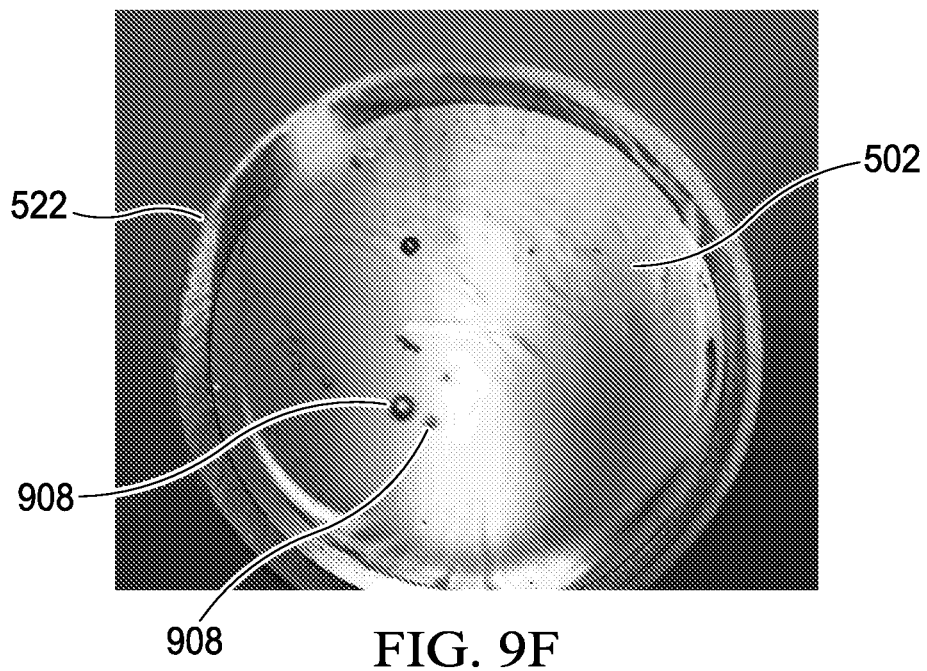
Figure 9G:
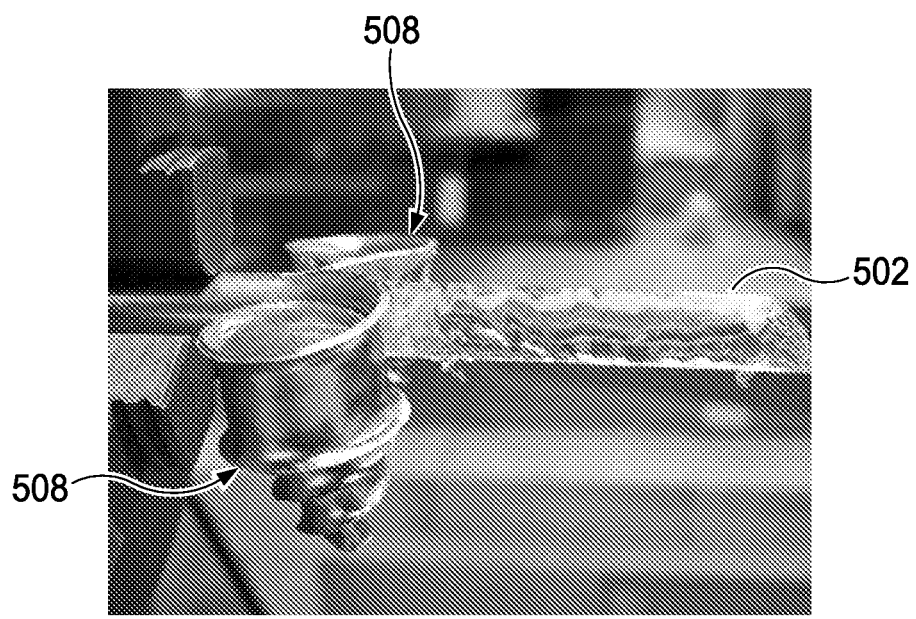

In FIG. 9E, there is a photo showing the sampling tube 508 with the glass sample 502 after cooling, solidification and annealing. In FIG. 9F, there is a photo showing an end view of the glass sample 502 (this particular sample was not annealed) located with the sampling tube's second end 522, where inclusions 908 can be seen and studied inside the sampling tube 502 without having to remove the glass sample 502 from the sampling tube 502. In FIG. 9G, there is a photo that the shows the glass sample 502 after the sampling tube's second end 522 has been cooled, cut and then peeled away from the glass sample 502. Removing the glass sample 502 from the sampling tube 508 is advantageous for obtaining a Blister Gas Analysis on blisters.

From the foregoing, one skilled in the art will appreciate that the glass sampling apparatus 200 and 500 and the methods described herein for using the glass sampling apparatus 200 and 500 to obtain the glass sample 202 and 502 from molten glass 204 and 504 within the glass melting vessel 206 and 506 has many advantages some of which are as follows:

1. The glass sampling apparatus 200 and 500 allows one to obtain a much larger glass sample 202 and 502 when compared to the glass samples 102a and 102b obtained by the traditional glass sampling apparatus 100. In addition, the glass sampling apparatus 200 and 500 enables one to obtain the glass sample 202 and 502 much deeper in the molten glass 204 and 504 when compared to the dip method using the traditional glass sampling apparatus 100.
1. The glass sampling apparatus 200 and 500 can be used to obtain glass samples 202 and 502 which can be used to diagnose and troubleshoot a range of defects such as inclusions, chemistry, and cords within the molten glass 204 and 504.
2. The glass sampling apparatus 200 and 500 can be used to obtain glass samples 202 and 502 which can be used to obtain an accurate estimate of the inclusion level in a known area of a glass melting system.
3. The glass sampling apparatus 200 and 500 can be used to sample glass in the melting vessel 810, the level probe standpipe 827, the finer to stir chamber 825, the stir chamber 830, the bowl 840, the inlet 855, or any free surface within a glass melting system.
4. The glass sampling apparatus 200 and 500 can be used to obtain glass samples 202 and 502 which can be used to study glass composition and oxidation state as a function of position in the glass manufacturing system 800 (e.g., the glass melting and delivery system).

Although several embodiments of the present invention have been illustrated in the accompanying Drawings and described in the foregoing Detailed Description, it should be understood that the invention is not limited to the disclosed embodiments, but is capable of numerous rearrangements, modifications and substitutions without departing from the invention as set forth and defined by the following claims.

The invention claimed is:

1. A glass sampling apparatus for obtaining a glass sample from molten glass within a glass melting vessel, the glass sampling apparatus comprising:

a sampling tube having a first end and a second end, where the second end is used to obtain the glass sample from the molten glass in the glass melting vessel;
a first valve;
a vacuum device; and
a tube network that couples the first end of the sampling tube to both the first valve and the vacuum device;
wherein the tube network includes a first tube which has one end coupled to the first end of the sampling tube and another end coupled to a first end of a multi-opening fitting, where the multi-opening fitting has a second end coupled to one end of a second tube which has one end coupled to one end of the vacuum device, and where the multi-opening fitting has a third end coupled to one end of a third tube which has another end coupled to one end of the first valve; and
wherein the multi-opening fitting is configured to allow a gas to freely pass therein between and out from the first end, the second end and the third end of the multi-opening fitting.

2. The glass sampling apparatus of claim 1, wherein the sampling tube is made of quartz, platinum, rhodium, palladium, iridium, rhenium, ruthenium, osmium, other refractory tube material, or some combination thereof.

3. The glass sampling apparatus of claim 1, wherein the vacuum device includes a syringe and plunger.

4. A glass sampling apparatus for obtaining a glass sample from molten glass within a glass melting vessel, the glass sampling apparatus comprising:

a sampling tube having a first end and a second end, where the second end is used to obtain the glass sample from the molten glass in the glass melting vessel;
a first valve;
a vacuum device;
a tube network that couples the first end of the sampling tube to both the first valve and the vacuum device;
a second valve coupled by the tube network between the first end of the sampling tube and both of the first valve and the vacuum device; and
wherein the tube network includes a first tube which has one end coupled to the first end of the sampling tube and another end coupled to a first end of the second valve which has a second end coupled to a first end of a multi-opening fitting, where the multi-opening fitting has a second end coupled to one end of a second tube which has another end coupled to one end of the vacuum device, and where the multi-opening fitting has a third end coupled to one end of a third tube which has another end coupled to one end of the first valve.

5. A glass sampling apparatus for obtaining a glass sample from molten glass within a glass melting vessel, the glass sampling apparatus comprising:

a sampling tube having a first end and a second end, where the second end is used to obtain the glass sample from the molten glass in the glass melting vessel;
a first valve;
a vacuum device;
a tube network that couples the first end of the sampling tube to both the first valve and the vacuum device;
a electrical isolation sleeve positioned around at least a portion of the sampling tube; and
a three-axis positioning stage including at least one rod extending therefrom and attached to the electrical isolation sleeve on the sampling tube, wherein the three-axis positioning stage is configured to move the second end of sampling tube into and out of the molten glass to obtain the glass sample from the glass melting vessel.

6. A method for obtaining a glass sample from molten glass within a glass melting vessel, the method comprising the steps of:
providing a glass sampling apparatus comprising:
a sampling tube having a first end and a second end, where the second end is used to obtain the glass sample from the molten glass in a glass melting vessel;
a first valve;
a vacuum device; and
a tube network that couples the first end of the sampling tube to both the first valve and the vacuum device;
wherein the tube network includes a first tube which has one end coupled to the first end of the sampling tube and another end coupled to a first end of a multi-opening fitting, where the multi-opening fitting has a second end coupled to one end of a second tube which has one end coupled to one end of the vacuum device, and where the multi-opening fitting has a third end coupled to one end of a third tube which has another end coupled to one end of the first valve; and
wherein the multi-opening fitting is configured to allow a gas to freely pass therein between and out from the first end, the second end and the third end of the multi-opening fitting; and
obtaining the glass sample from the molten glass in the glass melting vessel using the glass sampling apparatus.

7. The method of claim 6, further comprising the steps of:
cutting the sampling tube; and
peeling the sampling tube away from the glass sample.

8. The method of claim 6, wherein the obtaining step further comprises the steps of:
opening the first valve;
inserting the second end of the sampling tube into the molten glass within the glass melting vessel while the first valve is opened;
allowing the glass sample including at least one of surface molten glass and near surface molten glass from the molten glass to flow-up into the second end of the sampling tube while the first valve is opened;
closing the first valve; and
extracting the second end of the sampling tube with the glass sample located therein from the molten glass within the glass melting vessel while the first valve is closed.

9. The method of claim 6, wherein the sampling tube is made of quartz, platinum, rhodium, palladium, iridium, rhenium, ruthenium, osmium, other refractory tube material, or some combination thereof.

10. The method of claim 6, wherein the vacuum device includes a syringe and plunger.

11. The method of claim 6, wherein the glass melting vessel includes one of the following: a melting vessel, a level probe standpipe, a stir chamber, a finer to stir chamber tube, a bowl and an inlet.

12. A method for obtaining a glass sample from molten glass within a glass melting vessel, the method comprising the steps of:
providing a glass sampling apparatus comprising:
a sampling tube having a first end and a second end, where the second end is used to obtain the glass sample from the molten glass in a glass melting vessel;
a first valve;
a vacuum device; and
a tube network that couples the first end of the sampling tube to both the first valve and the vacuum device;
obtaining the glass sample from the molten glass in the glass melting vessel using the glass sampling apparatus; and
annealing the sampling tube and the glass sample.

13. A method for obtaining a glass sample from molten glass within a glass melting vessel, the method comprising the steps of:
providing a glass sampling apparatus comprising:
a sampling tube having a first end and a second end, where the second end is used to obtain the glass sample from the molten glass in a glass melting vessel;
a first valve;
a vacuum device; and
a tube network that couples the first end of the sampling tube to both the first valve and the vacuum device;
obtaining the glass sample from the molten glass in the glass melting vessel using the glass sampling apparatus; and
wherein the obtaining step further comprises the steps of:
closing the first valve;
inserting the second end of the sampling tube to a desired depth into the molten glass within the glass melting vessel while the first valve is closed;
opening the first valve;
allowing the glass sample including molten glass at the desired depth within the glass melting vessel to flow-up into the second end of the sampling tube while the first valve is opened;
closing the first valve;
operating the vacuum device to create a vacuum on top of the glass sample located inside the sampling tube while the first valve is closed;
extracting the second end of sampling tube with the glass sample located therein from the molten glass within the glass melting vessel while the first valve is closed and the vacuum device creates the vacuum on top of the glass sample located inside the sampling tube.

14. A method for obtaining a glass sample from molten glass within a glass melting vessel, the method comprising the steps of:
providing a glass sampling apparatus comprising:
a sampling tube having a first end and a second end, where the second end is used to obtain the glass sample from the molten glass in a glass melting vessel;
a first valve;
a vacuum device;
a tube network that couples the first end of the sampling tube to both the first valve and the vacuum device; and
a second valve coupled by the tube network between the first end of the sampling tube and both of the first valve and the vacuum device; and
obtaining the glass sample from the molten glass in the glass melting vessel using the glass sampling apparatus; and
wherein the obtaining step further comprises the steps of:
closing the first valve and the second valve;
inserting the second end of the sampling tube to a desired depth into the molten glass within the glass melting vessel while the first valve and the second valve are closed;
opening the first valve and the second valve;
allowing the glass sample including molten glass at the desired depth within the glass melting vessel to flow-up into the second end of the sampling tube while the first valve and the second valve are opened;

closing the first valve;
operating the vacuum device to create a vacuum on top of the glass sample located inside the sampling tube while the first valve is closed and the second valve is opened;
extracting the second end of the sampling tube with the glass sample located therein from the molten glass within the glass melting vessel while the first valve is closed, the second valve is opened, and the vacuum device creates the vacuum on top of the glass sample located inside the sampling tube.

15. A method for obtaining a glass sample from molten glass within a glass melting vessel, the method comprising the steps of:
providing a glass sampling apparatus comprising:
a sampling tube having a first end and a second end, where the second end is used to obtain the glass sample from the molten glass in a glass melting vessel;
a first valve;
a vacuum device;
a tube network that couples the first end of the sampling tube to both the first valve and the vacuum device; and
a second valve coupled by the tube network between the first end of the sampling tube and both of the first valve and the vacuum device; and
wherein the tube network includes a first tube which has one end coupled to the first end of the sampling tube and another end coupled to a first end of the second valve which has a second end coupled to a first end of a multi-opening fitting, where the multi-opening fitting has a second end coupled to one end of a second tube which has another end coupled to one end of the vacuum device, and where the multi-opening fitting has a third end coupled to one end of a third tube which has another end coupled to one end of the first valve; and
obtaining the glass sample from the molten glass in the glass melting vessel using the glass sampling apparatus.

16. The method of claim 15, wherein the obtaining step further comprises the steps of:
opening the first valve and the second valve;
inserting the second end of the sampling tube into the molten glass within the glass melting vessel while the first valve and the second valve are opened;
allowing the glass sample including at least one of surface molten glass and near surface molten glass from the molten glass to flow-up into the second end of the sampling tube while the first valve and the second valve are opened;
closing at least one of the first valve and the second valve; and
extracting the second end of the sampling tube with the glass sample located therein from the molten glass within the glass melting vessel while the at least one of the first valve and the second valve is closed.

17. A method for obtaining a glass sample from molten glass within a glass melting vessel, the method comprising the steps of:
providing a glass sampling apparatus comprising:
a sampling tube having a first end and a second end, where the second end is used to obtain the glass sample from the molten glass in a glass melting vessel;
a first valve;
a vacuum device; and
a tube network that couples the first end of the sampling tube to both the first valve and the vacuum device;
obtaining the glass sample from the molten glass in the glass melting vessel using the glass sampling apparatus; and
wherein the glass sampling apparatus further comprising:
a electrical isolation sleeve positioned around at least a portion of the sampling tube; and
a three-axis positioning stage including at least one rod extending therefrom and attached to the electrical isolation sleeve on the sampling tube; and
wherein the method further comprising the step of:
using the three-axis positioning stage to move the sampling tube into and out of the molten glass to obtain the glass sample from the glass melting vessel.

* * * * *